United States Patent [19]

Shturman

[11] Patent Number: 5,295,958
[45] Date of Patent: Mar. 22, 1994

[54] METHOD AND APPARATUS FOR IN VIVO HEART VALVE DECALCIFICATION

[75] Inventor: Leonid Shturman, Minneapolis, Minn.

[73] Assignee: Shturman Cardiology Systems, Inc., Minnetonka, Minn.

[21] Appl. No.: 680,705

[22] Filed: Apr. 4, 1991

[51] Int. Cl.⁵ .................................... A61M 29/00
[52] U.S. Cl. ................................. 604/96; 604/22; 604/53; 606/159; 606/194
[58] Field of Search ............... 606/191, 192, 194, 159, 606/160, 167–171, 180; 128/751, 757, 752, 772; 604/95–101, 103, 104, 22, 280, 264, 53

[56] References Cited

U.S. PATENT DOCUMENTS

| | | |
|---|---|---|
| 4,445,509 | 5/1984 | Auth . |
| 4,589,412 | 5/1986 | Kensey ................ 606/192 |
| 4,625,712 | 12/1986 | Wampler . |
| 4,784,636 | 11/1988 | Rydell ................ 606/194 |
| 4,790,813 | 12/1988 | Kensey ................ 606/159 |
| 4,817,586 | 4/1989 | Wampler ................ 600/16 |
| 4,846,152 | 7/1989 | Wampler et al. ................ 600/16 |
| 4,894,051 | 1/1990 | Shiber ................ 606/159 |
| 4,944,722 | 7/1990 | Carriker et al. ................ 600/16 |
| 4,979,951 | 12/1990 | Simpson ................ 606/159 |
| 4,990,134 | 2/1991 | Auth ................ 604/22 |
| 5,009,659 | 4/1991 | Hamlin et al. ................ 606/194 |
| 5,092,873 | 3/1992 | Simpson et al. ................ 606/170 |
| 5,100,424 | 3/1992 | Jang et al. ................ 606/159 |

FOREIGN PATENT DOCUMENTS

| | | | |
|---|---|---|---|
| 89/05611 | 6/1989 | World Int. Prop. O. ......... 606/170 |
| 90/07909 | 7/1990 | World Int. Prop. O. ......... 606/192 |

OTHER PUBLICATIONS

Bom, N., et al, "Early and Recent Intraluminal Ultrasound Devices," *International Journal of Cardiac Imaging*, 4:79–88, 1989.
Rutan, P. M., et al, "Initial Experience with the Hemopump," *Critical Care Nursing Clinics of North America*, vol. 1, No. 3, Sep. 1989, pp. 527–534.
Frazier, O. H., et al, "First Human Use of the Hemopump, a Catheter-Mounted Ventricular Assist Device," *Ann. Thorac. Surg.*, 1990:49:299–304.
Bashore, Thomas M., "Balloon Valvuloplasty," *Invasive Cardiology—Principles and Techniques*, pp. 145–147.
Block, Peter C. and Palacios, Igor F., "Percutaneous Mitral and Aortic Valvuloplasty," *The Practice of Cardiology*, 2d ed., Ch. 26, pp. 879–891.
Campbell, David B., et al, "'Conservative' Aortic Valve Intervention: Thwarted Again!," *JACC*, vol. 16, No. 3, Sep. 1990:631:2.
Shawl, Fayaz A., et al, "Percutaneous Cardiopulmonary Bypass Support in the Cathertization Laboratory: Technique and Complications," *American Heart Journal*, vol. 120, No. 1, Jul. 1990, pp. 195–203.
O'Keefe, J. H., et al, "Natural History of Candidates for Balloon Aortic Valvuloplasty," *Mayo Clin. Proc.*, Nov. 1987, 62:986–991.
Booth, D. C., "Aortic Stenosis and the Potential of Balloon Aortic Valvuloplasty," *Masters in Cardiology*, vol. 5, Spring 1988:11–13.
Levinson, J. R., et al, "Octogenarians With Aortic Stenosis," *Circulation*, vol. 80, No. 3, Sep. 1989 (Suppl. I):49–56.

(List continued on next page.)

*Primary Examiner*—C. Fred Rosenbaum
*Assistant Examiner*—Ronald Stright, Jr.
*Attorney, Agent, or Firm*—Gregory P. Kaihoi

[57] ABSTRACT

A method and apparatus for in vivo removal of calcified deposits from an aortic valve. The apparatus includes an anchoring balloon catheter fixatable across the aortic valve, a tool for removing the deposits, and attachment means for securing the tool with respect to the anchoring balloon and the aortic valve. The method involves advancing an anchoring balloon catheter through the aorta and positioning it across the aortic valve, inflating the anchoring balloon to fixate it with respect to the aorta and aortic valve, and then operating a deposit removal tool secured to the anchoring balloon to remove the deposits.

55 Claims, 36 Drawing Sheets

OTHER PUBLICATIONS

Fremes, S. E., et al, "Valvular Surgery in the Elderly," *Circulation*, vol. 80, No. 3, Sep. 1989 (Suppl. I):77–90.

Craver, J. M., et al, "Predictors of Mortality, Complications, and Length of Stay in Aortic Valve Replacement for Aortic Stenosis," *Circulation*, vol. 78, No. 3, Sep. 1988 (Suppl. I):85–90.

Enright, L. P., et al, "Aortic Debridement—Long-term Follow-up," *Circulation*, vols. 43 and 44, May 1971 (Suppl. I):68–72.

Safian, R. D., et al, "Postmortem and Intraoperative Balloon Valvuloplasty of Calcific Aortic Stenosis in Elderly Patients: Mechanism of Successful Dilation," *JACC*, vol. 9, No. 3, Mar. 1987:655–60.

Cribier, A., et al, "Feasibility and Safety of Balloon Aortic Valvuloplasty in Patients Under 70 Years of Age," *Circulation*, 1987;76 (Suppl. 4).

Holmes, D. R., Jr., et al, "The Safety and Efficacy of a Dual-balloon Approach During Percutaneous Aortic Balloon Valvuloplasty," *Circulation*, vol. 76, Oct. 1987 (Suppl. 4).

Kuntz, R. E., et al, "Follow-up of Balloon Aortic Valvuloplasty: Results in 192 Cases," *JACC*, vol. 13, No. 2, Feb. 1989, 16A.

Feldman, T., et al, "Second Dilatation for Restenosis Following Successful Balloon Aortic Valvuloplasty: Results, Pathology and Mechanism," *JACC*, vol. 13, No. 2, Feb. 1989, 17A.

Davidson, C. J., et al, "Failure of Balloon Aortic Valvuloplasty to Result in Sustained Clinical Improvement in Patients With Depressed Left Ventricular Function," *JACC*, vol. 13, No. 2, Feb. 1989, 17A.

Spielberg, C., et al, "One-Two Year Follow-up After Primarily Successful Valvuloplasty for Calcified Aortic Stenosis," *JACC*, vol. 13, No. 2, Feb. 1989, 16A.

"Aortic Valvuloplasty Gives Major Gain for Small, Select Pt Subpopulation," *The Newspaper of Cardiology*, Mar. 1990:17.

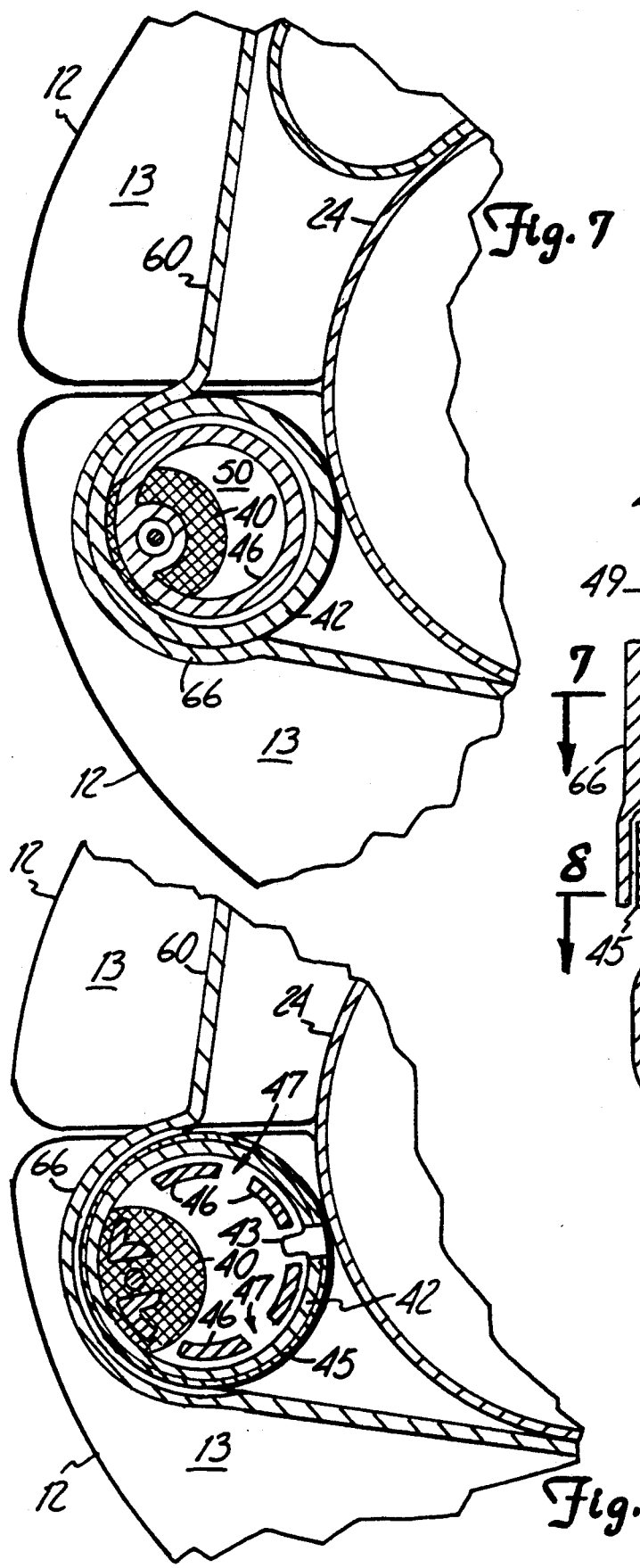

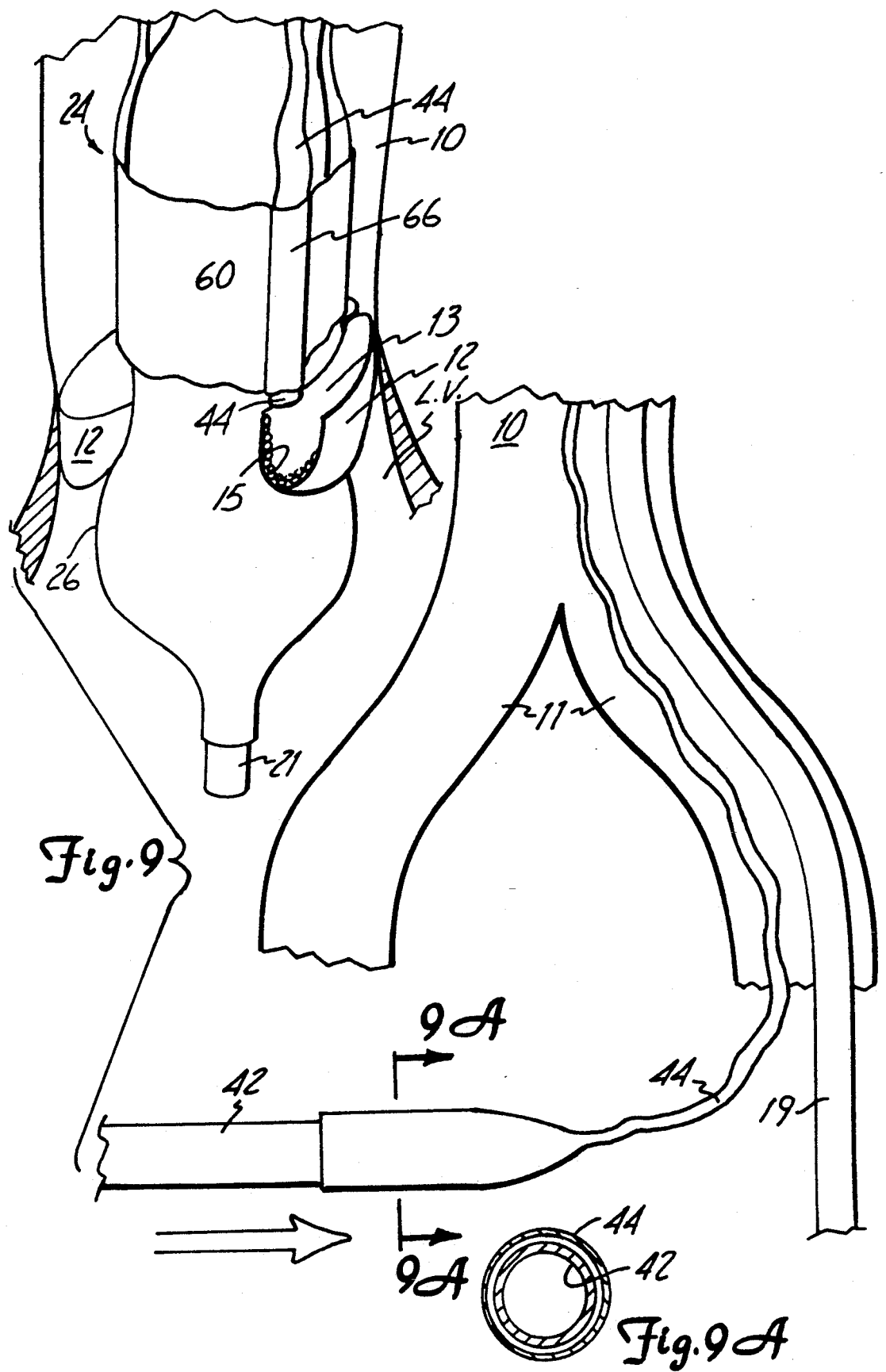

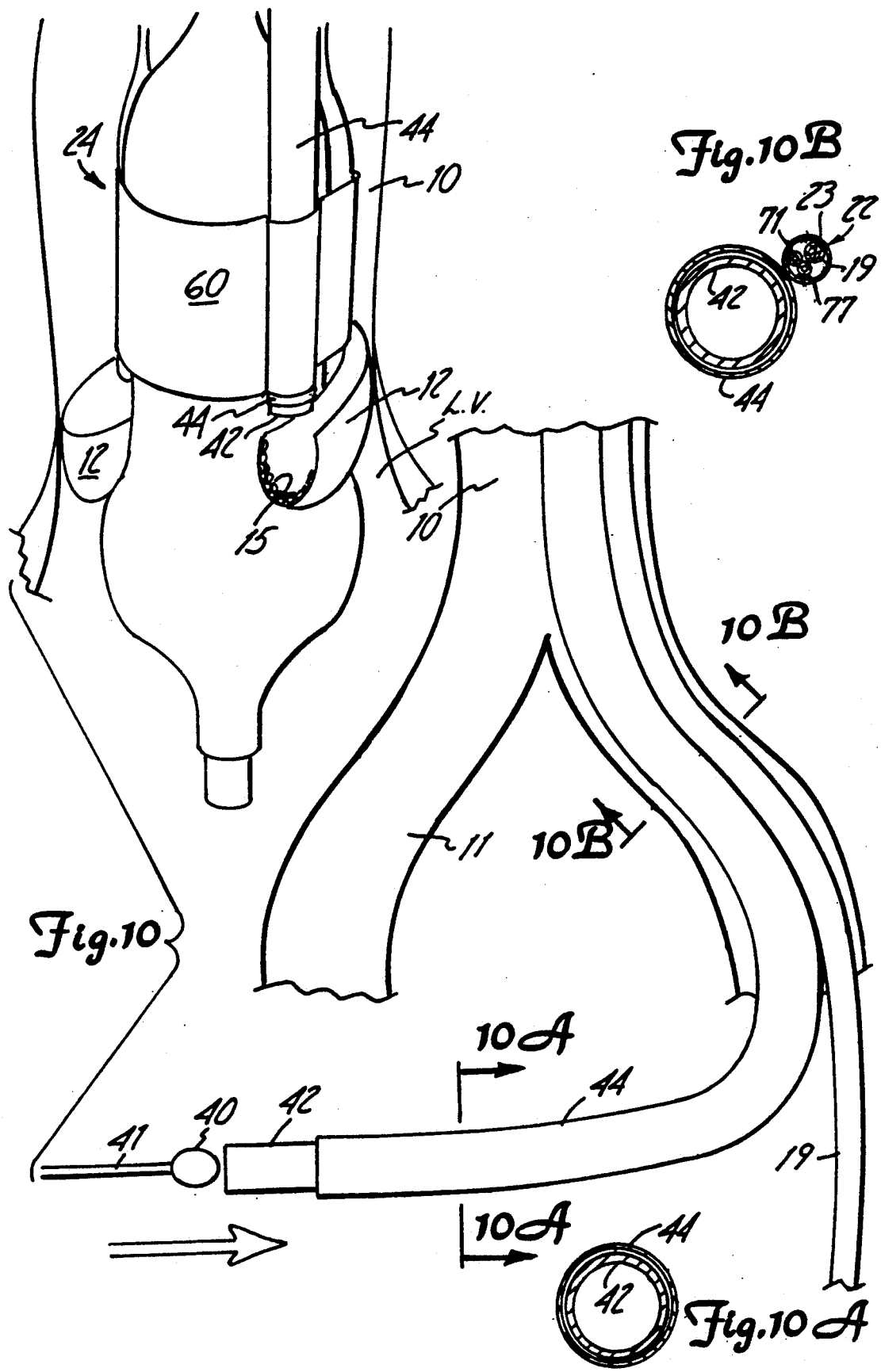

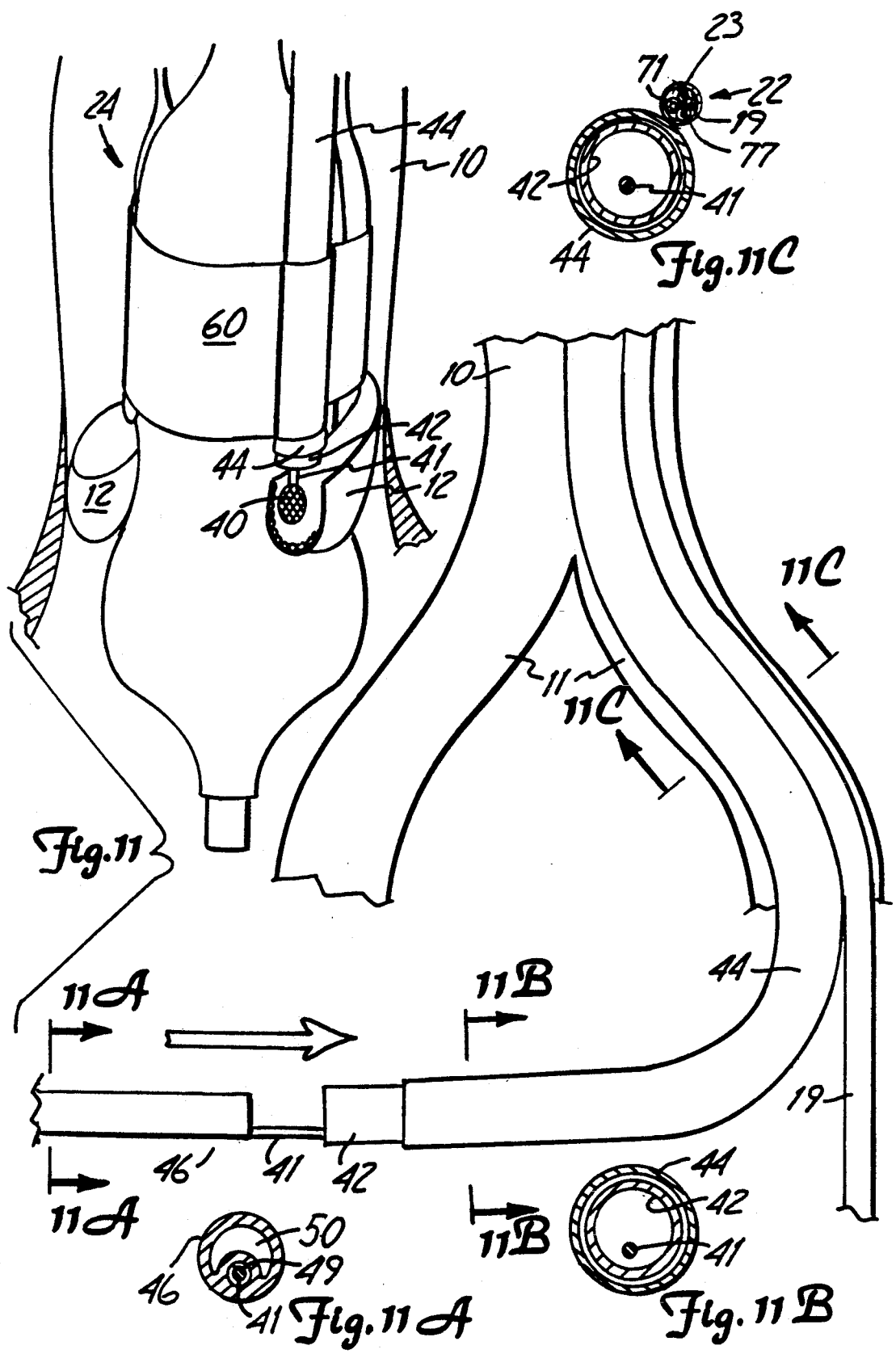

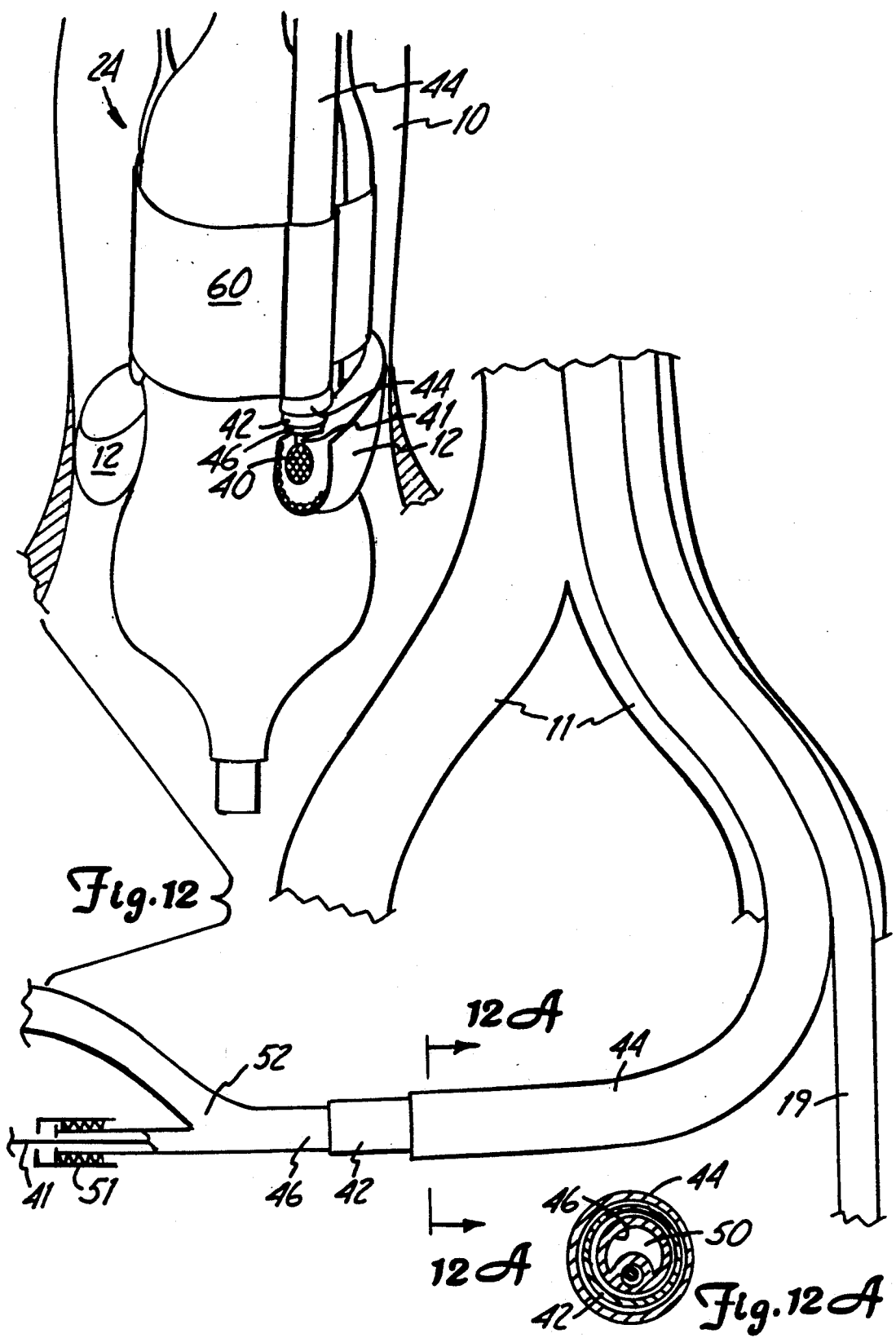

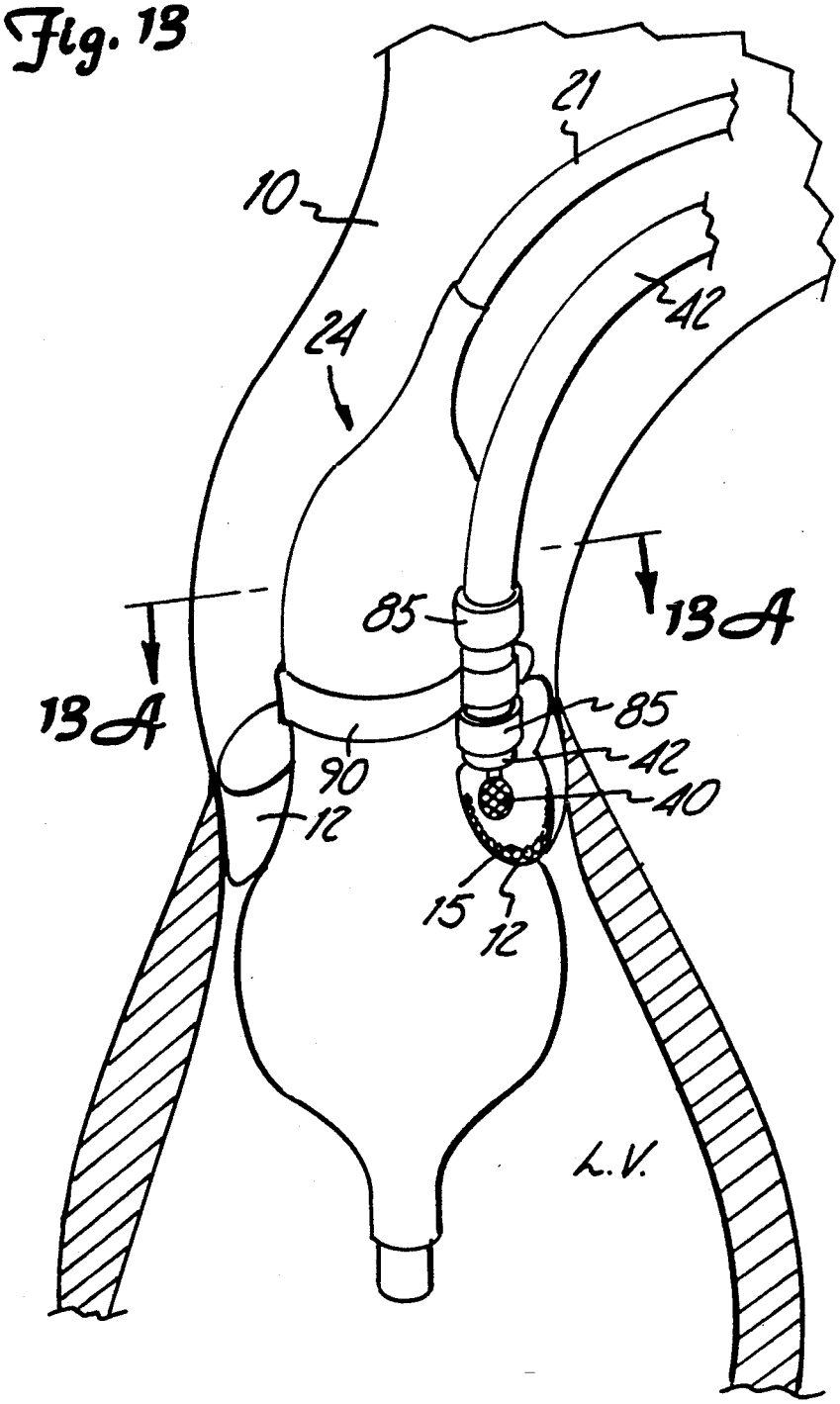

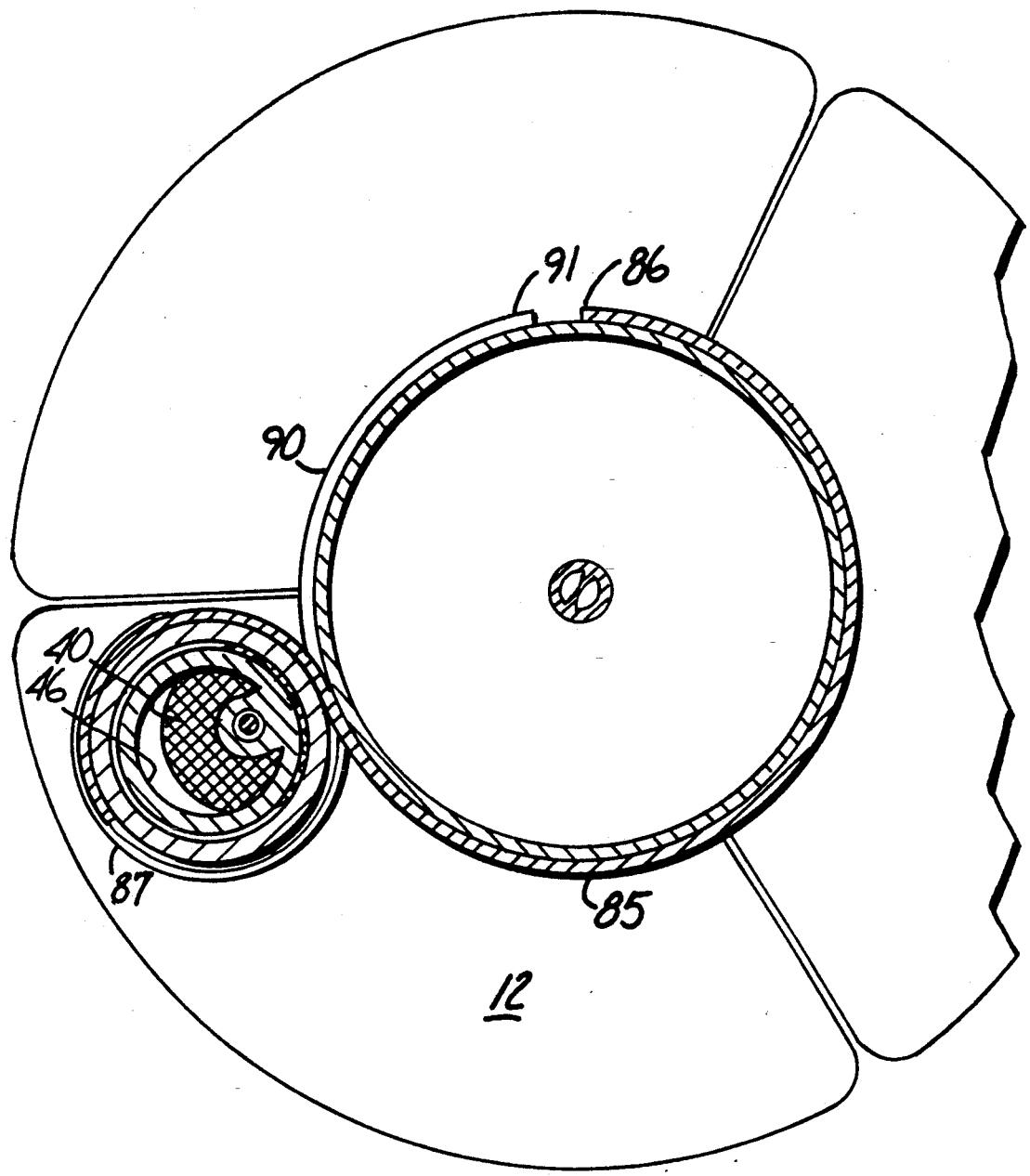

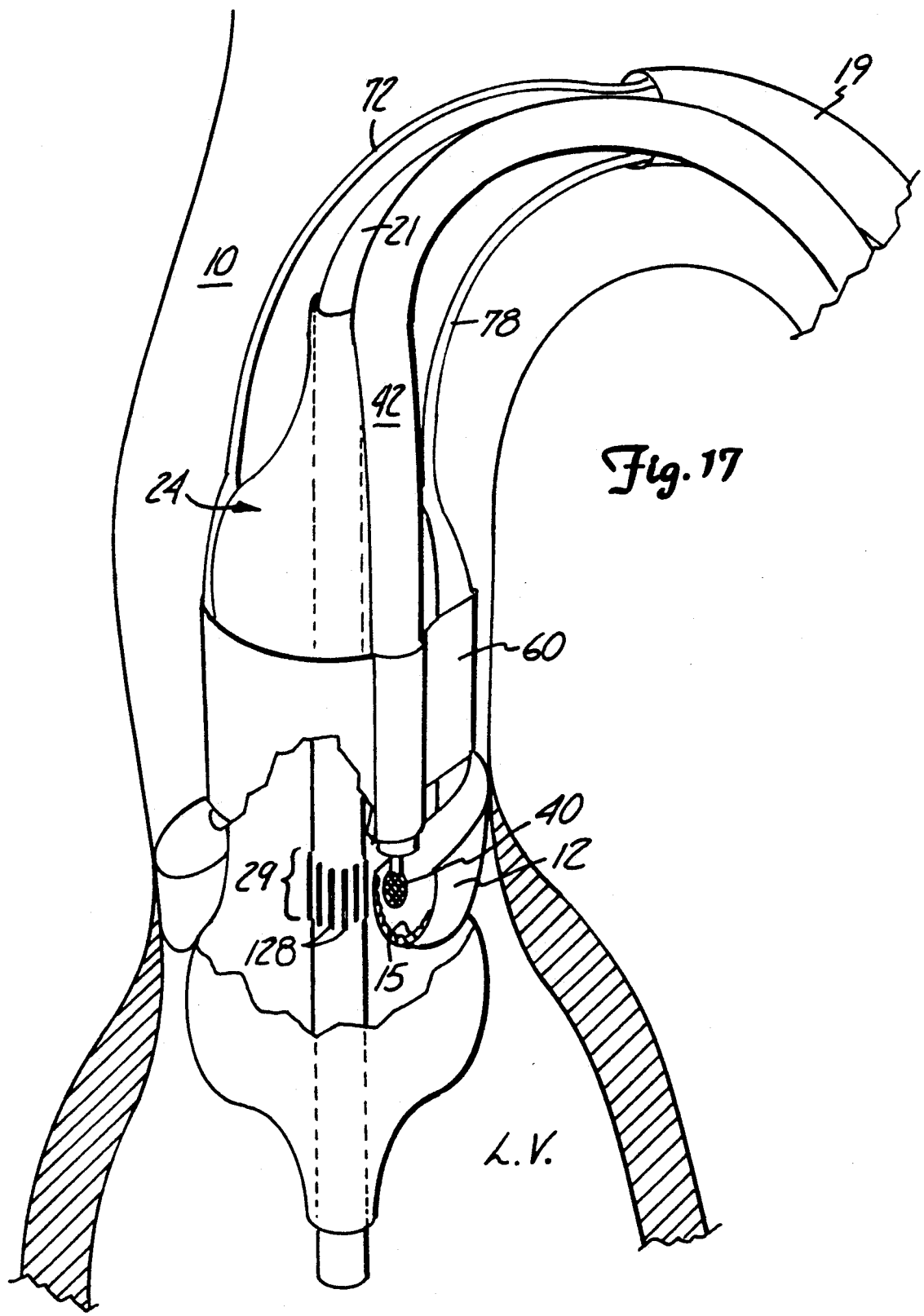

METHOD AND APPARATUS FOR IN VIVO HEART VALVE DECALCIFICATION

FIELD OF THE INVENTION

The invention relates to a method and apparatus for removing, in vivo, calcified deposits from heart valves.

BACKGROUND OF THE INVENTION

Calcific aortic stenosis (i.e., the buildup of calcified deposits on the superior surface of the aortic heart valve) accounts for a large percentage of aortic stenosis cases. This condition is characterized by the buildup of calcified nodules on the upper or superior surface of the aortic valve leaflets. These nodules decrease the flexibility of the leaflets, thereby limiting their mobility and capacity to fully open to permit adequate blood flow. Absent anatomic correction, advanced aortic stenosis carries a poor prognosis.

Three techniques have been employed to correct aortic stenosis: valve replacement, intraoperative decalcification (debridement) of the heart valve, and balloon valvuloplasty.

Valve replacement during open heart surgery is currently standard therapy for symptomatic aortic stenosis. Ten year survival rates for isolated aortic valve replacement are generally very good, even in elderly patients. However, this technique requires that the patient be healthy enough to undergo open heart surgery. The operative mortality for this procedure, particularly among the elderly, is also significant—variously reported at between about 5% and 12%. In addition, a patient receiving a replacement valve typically must take anticoagulation drugs for the rest of his or her life—not all patients are capable of doing this. Moreover, some patients have an aortic root that is not large enough to easily accommodate conventional replacement valves. Thus, there are a significant number of patients for whom valve replacement is either impossible, impractical, or undesirable.

Intraoperative mechanical debridement (decalcification) of the aortic valve to treat aortic stenosis was successfully used for many years prior to the advent of mechanical replacement valves. In this technique, the aorta is entered surgically (as in a valve replacement procedure) but rather than replace the valve the surgeon manually removes the calcified deposits, using suitable surgical tools. The debridement techniques, although for some time completely forsaken in favor of valve replacement procedures, has enjoyed some recent revival, particularly for patients having a small aortic root and/or contraindications for anticoagulation therapy. In addition to mechanical tools, recently ultrasonic debridement has also been demonstrated to be effective to remove calcific deposits. Nevertheless, these techniques still require the patient to be healthy enough to survive and recuperate from thoracic surgery, and involve all of the costs and risks attendant with such surgery.

The third technique for correcting aortic stenosis involves percutaneous balloon aortic valvuloplasty (BAV). In this procedure, an inflatable balloon catheter is advanced to the aortic valve and inflated to compress and fracture the calcified nodules in an attempt to increase leaflet mobility. Although this procedure eliminates many of the risks and disadvantages attendant with the preceding two techniques, restenosis is very common within one year, limiting the technique's usefulness to temporarily mitigating symptom for those patients who are poor surgical candidates or refuse surgery.

SUMMARY OF THE INVENTION

The invention provides a method and apparatus for in vivo removal of calcified deposits from an aortic valve. The apparatus includes an anchoring balloon catheter fixatable across the aortic valve, a tool for removing the deposits, and attachment means for securing the tool with respect to the anchoring balloon and the aortic valve.

The attachment means preferably includes means for positioning the deposit removal tool with respect to the anchoring balloon. In one embodiment the distal end of a guiding catheter is secured to the anchoring balloon, and positioning of the tool is accomplished by selectively moving the distal end of the guiding catheter about the anchoring balloon and by moving the tool around within the guiding catheter.

One embodiment for securing the guiding catheter with respect to the anchoring balloon while allowing selective movement of the guiding catheter employs a circumferential band having first and second ends respectively attached to the anchoring balloon, with the distal end of the guiding catheter attached to an intermediate portion of the band. Positioning balloons are interposed between the circumferential band and the anchoring balloon. The positioning balloons work in concert, so that as one balloon is inflated, the other is deflated, thereby changing the relative position of the intermediate portion of the band and the associated distal en of the guiding catheter. Thus, when a first of the balloons is being inflated (with the second balloon being simultaneously deflated), the distal end of the guiding catheter will move clockwise about the anchoring balloon, and when the second balloon is being inflated (with the first balloon being simultaneously deflated), the distal end of the guiding catheter will move counterclockwise about the anchoring balloon.

The deposit removal tool may be positioned within the guiding catheter by providing a coaxial positioning catheter within the guiding catheter. The positioning catheter preferably includes an off-center lumen in which the elongated shaft of the removal tool is closely received. Thus, by rotating the positioning catheter within the guiding catheter, the position of the removal tool can be selectively controlled.

The removal tool may comprise any effective device, including any one of a variety of rotatable cutting, scraping or abrading devices, an ultrasonic vibrations generator or a wire capable of conveying ultrasonic vibrations and being connected to an ultrasonic vibrations generator, an optical fiber connected to a laser outside of the body, a pair of electrodes connected to a high voltage source outside of the body, or any other suitable device.

In a modified embodiment of the invention, the anchoring balloon catheter utilized in the invention comprises an inflatable tube that has a proximal, generally straight portion, and a distal, helically coiled portion. The turns of the helical coil may be spaced from one another slightly, or successive turns may abut one another. Means may also be provided for securing the turns of the coil to one another, such as by providing an outer or inner skin to which the turns adhere.

The method of the invention involves removing, in vivo, deposits from an aortic valve's superior surface. The method comprises the steps of advancing an anchoring balloon catheter through the aorta and positioning it across the aortic valve, inflating the anchoring balloon to fixate it with respect to the aorta and aortic valve, and then operating a deposit removal tool secured to the anchoring balloon to remove the deposits.

BRIEF DESCRIPTION OF THE DRAWINGS

FIG. 6 is a cross-sectional broken away view of a modified embodiment of the invention;

FIG. 7 is a cross-sectional view of FIG. 6 taken along line 7—7 thereof;

FIG. 8 is a cross-sectional view of FIG. 6 taken along line 8—8 thereof;

FIG. 9 is a somewhat schematic representation of another embodiment of the apparatus of the invention in the process of being introduced into a patient;

FIG. 9A is a cross-sectional view of FIG. 9, taken along line 9A—9A thereof;

FIG. 10 is a view similar to FIG. 9 after the guiding catheter has been introduced into the otherwise flaccid sheath;

FIGS. 10A and 10B are cross-sectional views of FIG. 10, taken respectively across lines 10A—10A and 10B—10B thereof;

FIG. 11 is a view similar to FIG. 9 after the tool has been introduced into the guiding catheter;

FIGS. 11A, 11B and 11C are cross-sectional views of FIG. 11, taken respectively across lines 11A—11A, 11B—11B and 11C—11C thereof;

FIG. 12 is a view similar to FIG. 9 after the positioning catheter has been introduced into the guiding catheter over the tool shaft;

FIG. 12A is a cross-sectional view of FIG. 12, taken across line 12A—12A thereof;

FIG. 13 is a perspective view of another modified embodiment of the invention;

FIG. 14 is a cross-sectional view similar to FIG. 13B showing a modified embodiment of the invention;

FIG. 17 is a perspective view of yet another embodiment of the invention;

BEST MODE FOR CARRYING OUT THE INVENTION

Figure 1:
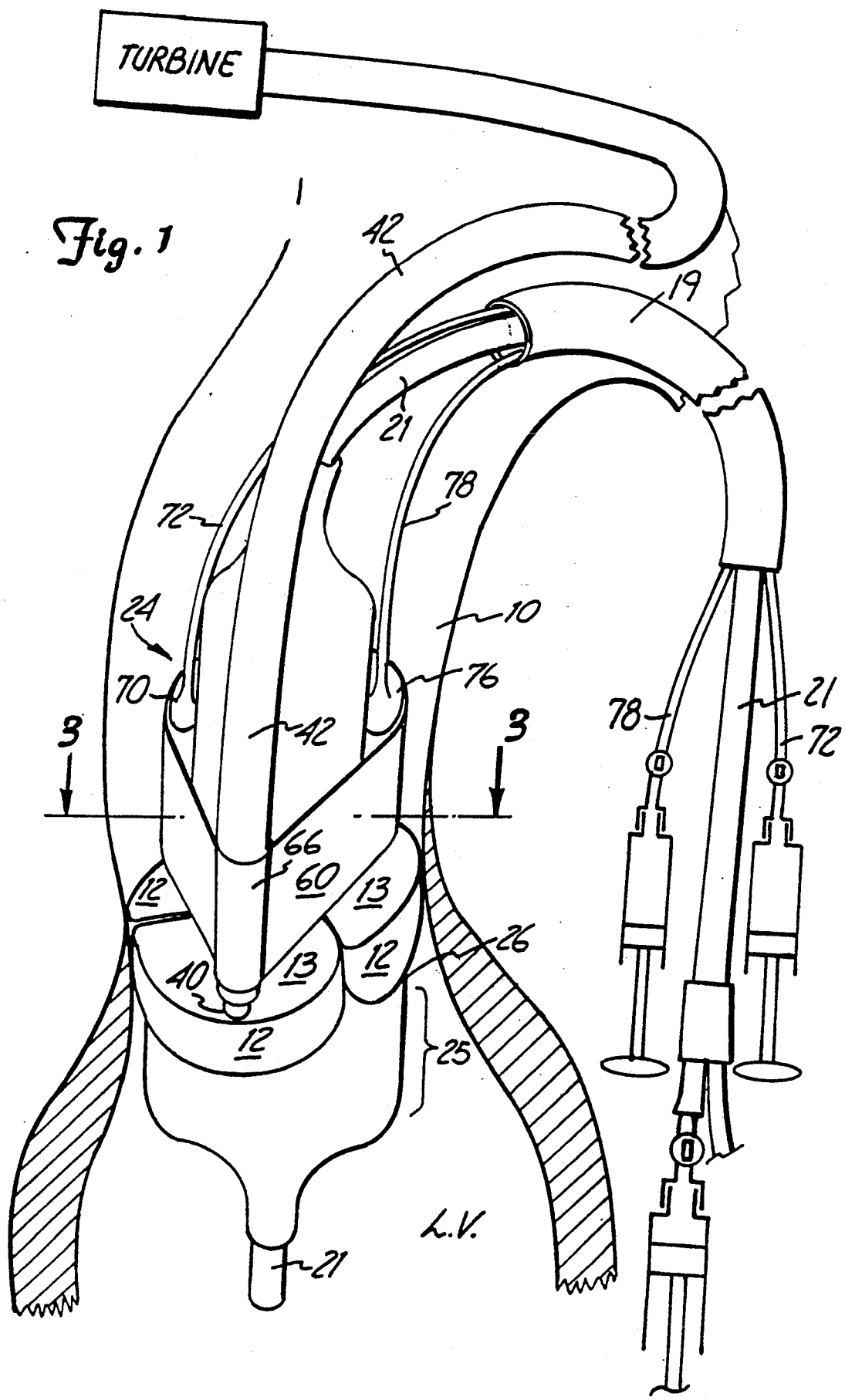
FIG. 1 is a perspective view in partial cross-section of the apparatus of the invention fixated in the aortic valve of a heart.
Figure 2:
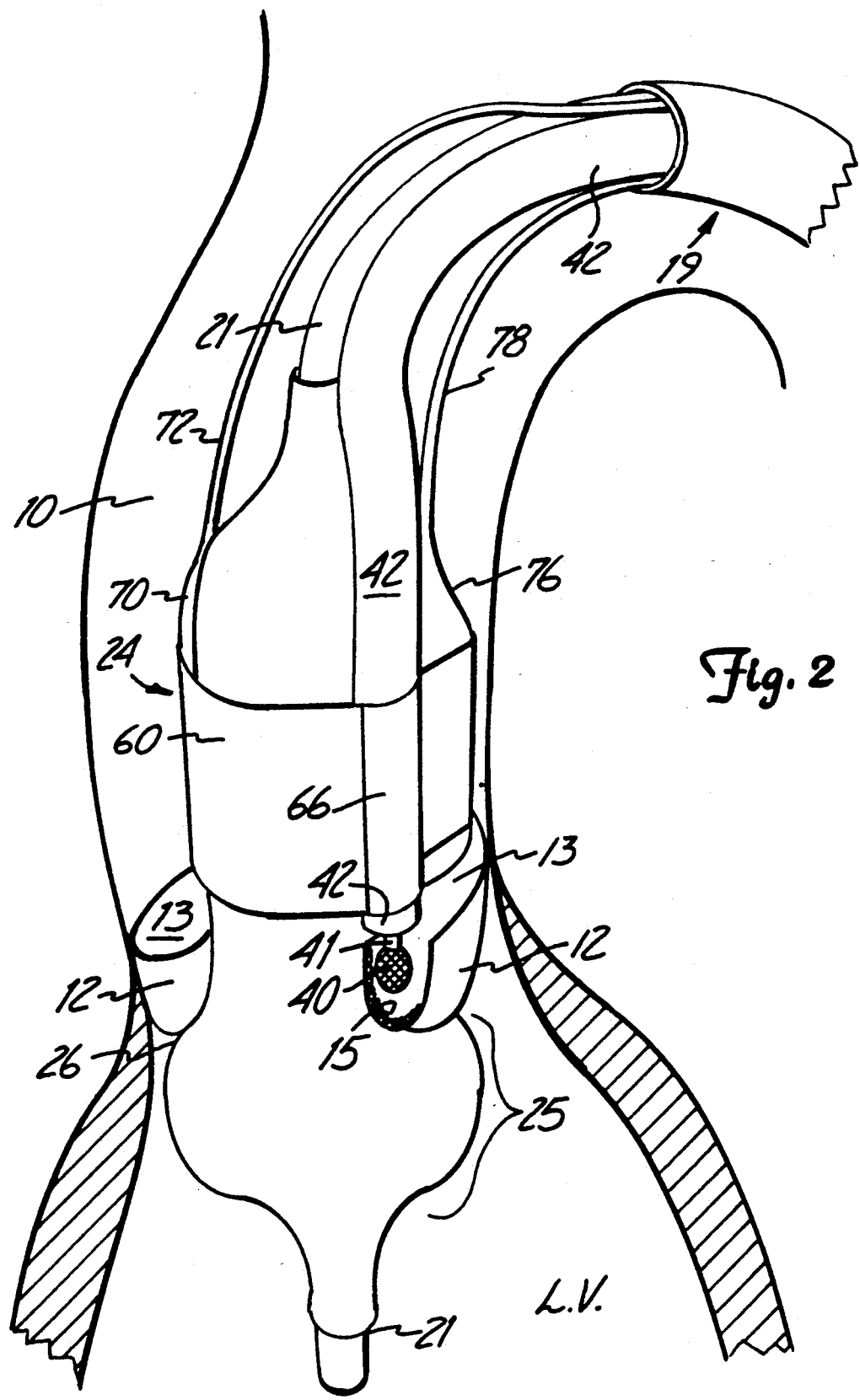
FIG. 2 is a perspective view in partial cross-section similar to FIG. 1 with one of the valve leaflets removed for clarity and with the guiding catheter shown in a moved position.

FIG. 1 shows in perspective, partial cross-sectional view an anchoring balloon catheter 24 of the invention secured in the aorta 10, with its distal portion 25 inserted past the leaflets 12 of the aortic valve. In FIG. 2, a portion of the valve leaflets 12 in the foreground has been omitted to reveal better the position and shape of the distal portion 25 of the anchoring balloon catheter 24 and the deposits 15 on the superior surface 13 of the leaflets. In this view, it can be seen that the distal portion 25 of the anchoring balloon is preferably of a larger diameter, having a shoulder 26 that contacts the inferior surface of the valve leaflets 12 to accurately and securely position the anchoring balloon 24, with respect to the valve leaflets 12, providing support to the leaflets to stabilize their positions and to outline the inferior surface of the leaflets 12 in contact with the balloon inflated with radiographic contrast solution. The anchoring balloon catheter 24 also includes a central catheter 21 having preferably at least a pair of lumens, one 22 for passage of the anchoring balloon catheter 24 over a guide wire (not shown) and/or injection or withdrawal of fluids therethrough, and a second 23 for inflation of the balloon 24.

Attachment means is provided to secure a deposit removal tool 40 to the inflatable anchoring balloon catheter 24. The attachment means may comprise a variety of configurations. A preferred embodiment is depicted in FIGS. 1-5. In this embodiment, the attachment means includes means for selectively positioning the deposit removal tool 40 with respect to the anchoring balloon 24 so that the physician can guide the tool 40 carefully to the calcification deposit 15 which is to be removed. Again, the preferred embodiment illustrated in FIGS. 1-5 shows a preferred mechanism for achieving this selective control.

In this preferred embodiment, a circumferential band 60 having first and second ends 62 and 64, respectively, is attached to the anchoring balloon 24. The circumferential band 60 also includes an intermediate portion 66, which is attached to a guiding catheter 42. The deposit removal tool 40 in turn is disposed within the guiding catheter 42.

Figure 3:
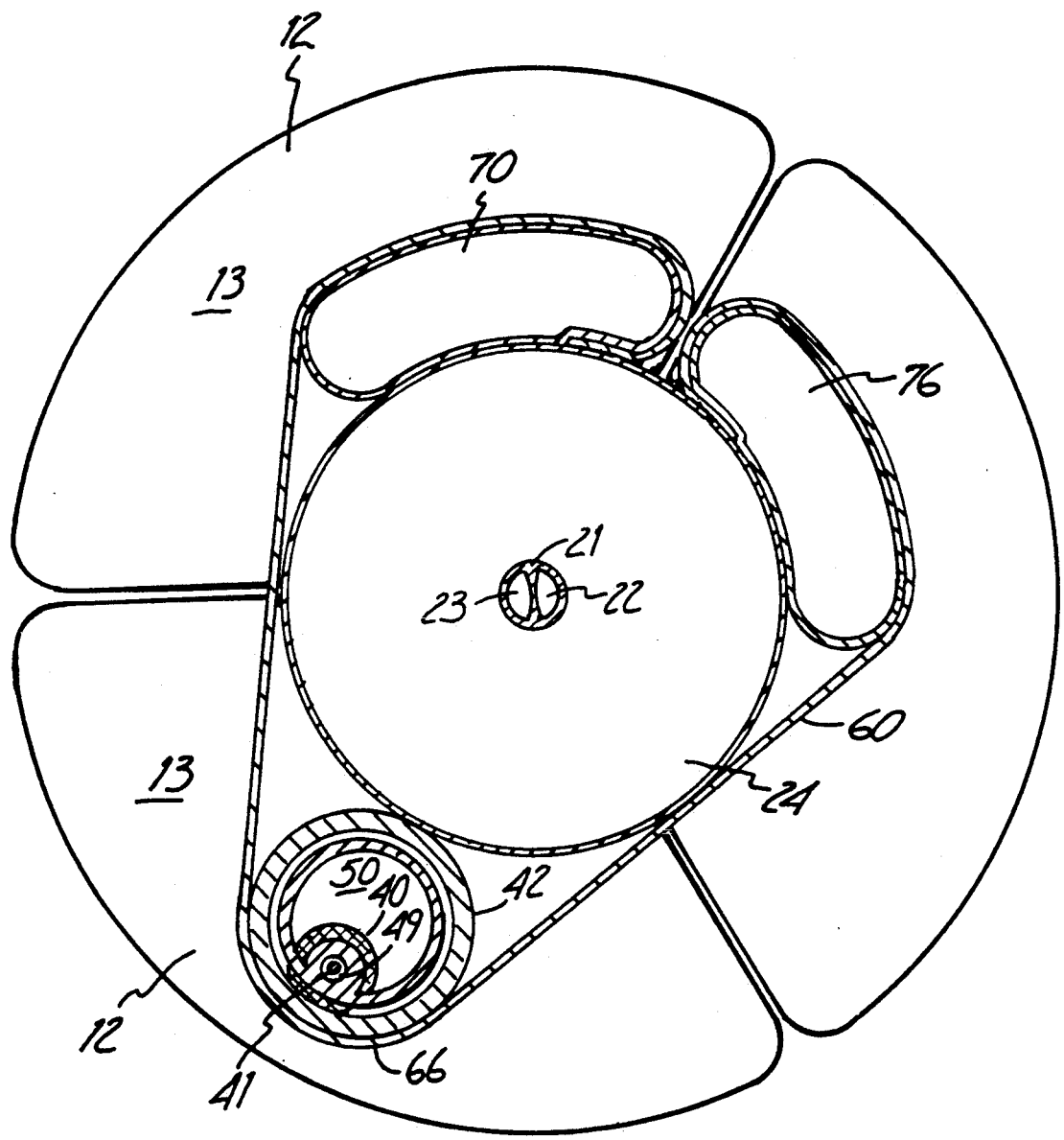
FIG. 3 is a cross-section of FIG. 1 taken along line 3—3 thereof.
Figure 4:
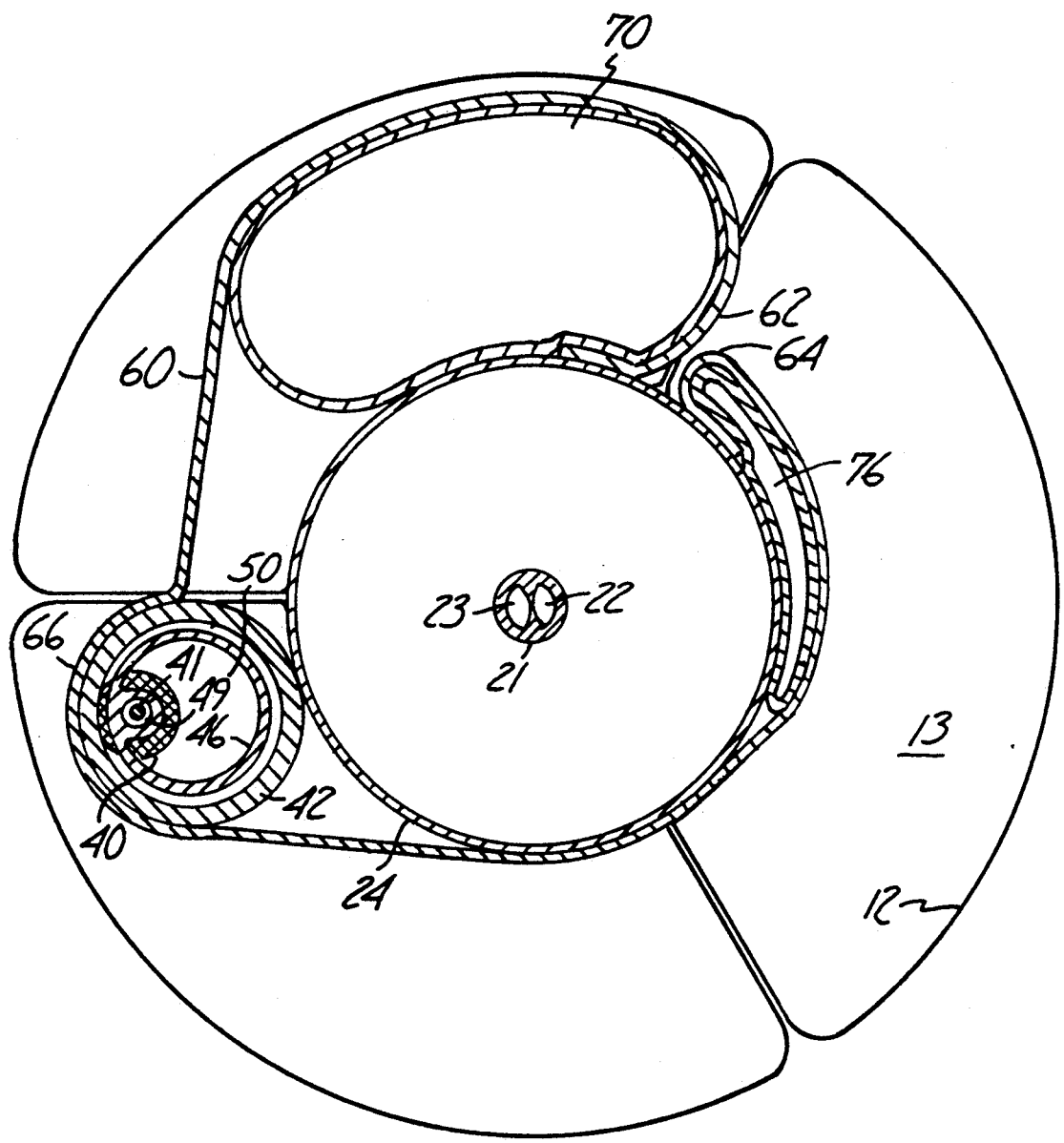
FIG. 4 is a cross-sectional view similar to FIG. 3 shown in a moved position.
Figure 5:
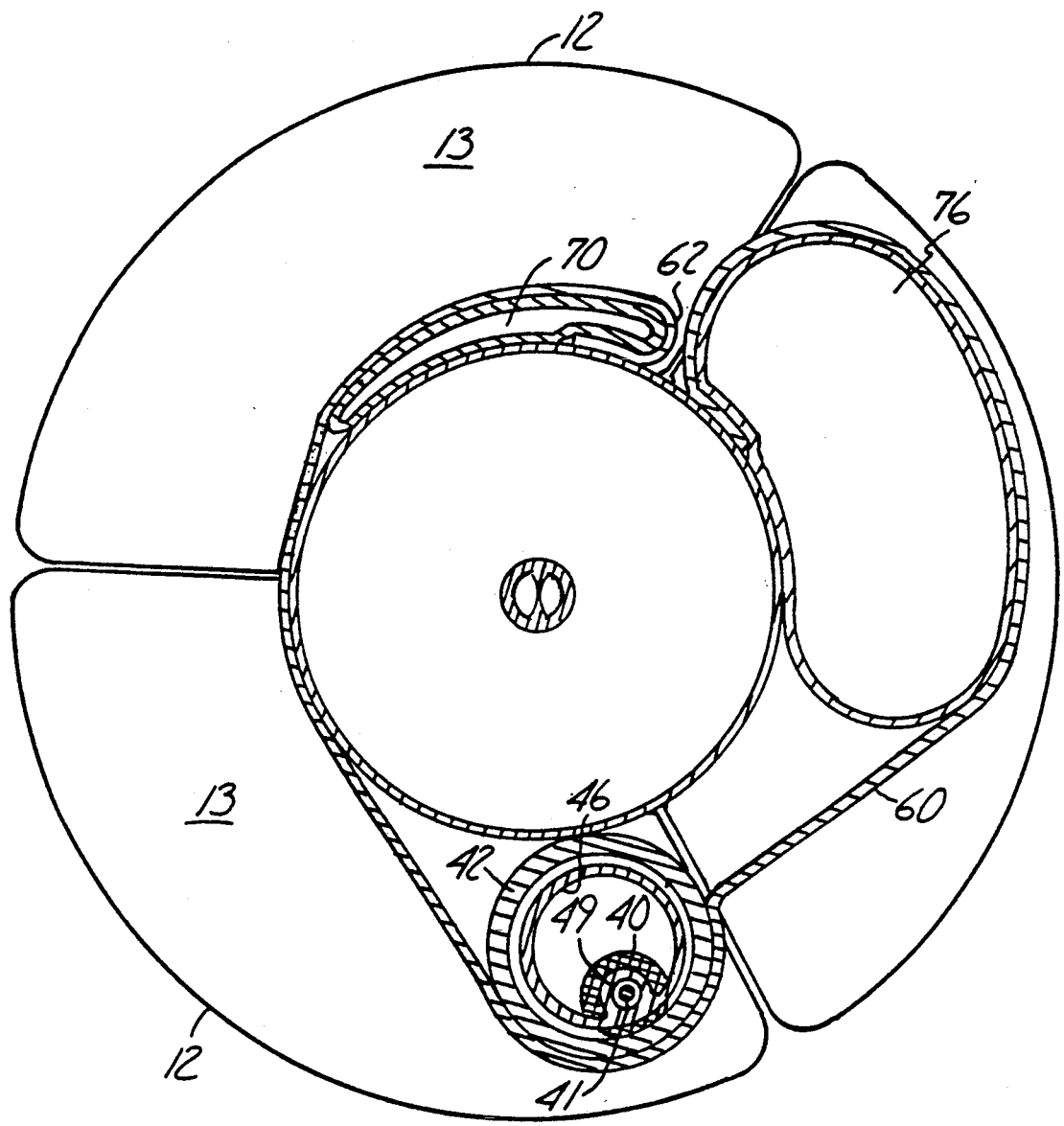
FIG. 5 is another cross-sectional view similar to FIG. 3 showing a second moved position.

As mentioned above, preferably means is provided for selectively moving the guiding catheter 42 about the periphery of the anchoring balloon 24. In this preferred embodiment, a pair of positioning balloons 70 and 76 are disposed between the circumferential band 60 and the anchoring balloon 24, each located adjacent the ends 62 and 64 of the circumferential band 60. As illustrated in FIGS. 3-5, the guiding catheter 42 can be moved about the periphery of the anchoring balloon 24 by selectively inflating and deflating the positioning balloons 70 and 76.

In FIG. 3, both of the positioning balloons 70 and 76 are partially inflated, and the guiding catheter 42 is in a generally central position. In FIG. 4, one of the positioning balloons 70 has been fully inflated and the other positioning balloon 76 deflated, causing the guiding catheter 42 to have moved to its most clockwise location. In FIG. 5, the first positioning balloon 70 is fully deflated, and the second positioning balloon 76 is fully inflated, causing the circumferential band 60 to pull the guiding catheter 42 to its most counterclockwise position. Thus, by selectively inflating and deflating the positioning balloons 70 and 76, the guiding catheter 42 can be moved through a range of positions about the anchoring balloon 24. The size of the positioning balloons and the diameter of the anchoring balloon will dictate what total range of motion is possible. Preferably, the range of motion should be at least about 120°, allowing the deposit removal tool 40 to fully service on of the three leaflets 12 of the aortic valve without repositioning the anchoring balloon 24. To remove deposits from the other leaflets 12, the anchoring balloon 24 can be partially deflated and then rotated to a new position corresponding to one of the other leaflets 12.

FIGS. 3-8 depict a secondary positioning means that allows some control over the radial position of the deposit removal tool 40. In this embodiment, a positioning catheter 46 is disposed within the guiding catheter 42. The positioning catheter 46 includes an off-center lumen 49 in which the shaft 41 of the deposit removal tool 40 is carried. By rotating the positioning catheter 46 with respect to the guiding catheter 42, the deposit removal tool 40 can be adjusted radially inwardly and outwardly with respect to the anchoring balloon 24. Some limited control over the circumferential position of the tool 40 is also provided.

FIGS. 6-8 illustrate a particularly preferred embodiment in which the positioning catheter 46 includes indexing slots 47 at its distal end. The guiding catheter 42 in turn carries a tab 43 extending radially inwardly (the tab 43 may, e.g., extend radially inwardly from a metal ring 45 carried by the guiding catheter 42). As the positioning catheter 46 is advanced through the guiding catheter 42 to its most distal position, the tab 43 of guiding catheter 42 will engage a corresponding slot 47 in the positioning catheter 46. This prevents rotational movement of the positioning catheter 46 with respect to the guiding catheter as the tool is being utilized. Where it is desired to change the rotational position of the positioning catheter 46, it can be withdrawn slightly, rotated, and then again advanced to engage the tab 43 in the desired slot 47 corresponding to the desired position.

FIGS. 9-12 illustrate another modification of the invention which includes a collapsable sheath 44, and illustrate its use in the process of introducing the device of the invention into the patient. In FIG. 9, the aorta 10 is shown schematically dividing into the left and right iliac arteries 11. The anchoring balloon catheter 24 with its catheter 21 has been inserted into the iliac artery 11, and advanced through the aorta to the aortic valve, where the anchoring balloon 24 is inflated. In this embodiment, a flaccid sheath 44 is connected directly to the circumferential band 60. This flaccid sheath allows final assembly of the entire unit inside the body—i.e., the anchoring balloon with the flaccid sheath 44, the circumferential band 60 and the positioning balloons 70 and 76 (all deflated and furled about the catheter 21 of the anchoring balloon 24) can first be inserted into the aorta 10 via the iliac artery 11. The guiding catheter, positioning catheter and deposit removal tool can then be inserted, after the anchoring balloon catheter is in position. The flaccid nature of this sheath 44 therefore allows the deflated anchoring balloon 24 with attachment means to be furled into a relatively small diameter unit for insertion through the narrower iliac artery 11 into the wider aorta 10. Once the anchoring balloon 24 has entered the aorta 10 (and, preferably, reached its position in the aortic valve), the anchoring balloon 24 can be inflated and the rest of the unit assembled by inserting the guiding catheter 42 through the sheath 44 to its position adjacent the anchoring balloon 24, followed by the deposit removal tool and the positioning catheter. To ease insertion of the guiding catheter into the sheath 44, the sheath can be of a larger diameter proximally, narrowing at its most distal portion to a diameter that closely receives the guiding catheter therein.

In FIG. 9, the guiding catheter 42 has been advanced only slightly into the sheath 44. In FIG. 10, the guiding catheter 42 is fully advanced, and the deposit removal tool 40 is about to be introduced. Note that FIGS. 10A and 10B illustrate the cross-sectional configuration of the device, and show catheter 19 with four lumens—one each 71 and 77 for inflating and deflating the positioning balloons 70 and 76, one 23 for inflating the anchoring balloon itself, and one 22 for passing through a guide wire or injecting or withdrawing fluids such as contrast or blood. The catheter 19 is formed from catheter 21 of the anchoring balloon catheter 24 and catheters 72 and 78 of the positioning balloons 70 and 76, respectively.

In FIG. 11 the deposit removal tool 40 has been fully advanced through the guiding catheter 42 and the positioning catheter 46 is about to be advanced over the shaft 41 of the deposit removal tool 40. FIG. 11A depicts the tool's shaft 41 closely received in the off-center lumen 49 of the positioning catheter 46. FIG. 12 shows the positioning catheter 46 fully advanced through the guiding catheter 42. A "Y" connector 52 may be provided on the proximal end of the positioning catheter 46 to allow fluid to be injected or withdrawn through the main lumen 50 of the positioning catheter 46, while the elongated shaft 41 of the tool 40 exits through a sealing fitting 51. In most applications, the main lumen 50 will be utilized to withdraw fluid from the area immediately adjacent the deposit removal tool, thereby removing any particles or debris cut away by the tool. This lumen 50 may also be used, however, for injecting fluids, such as contrast solutions used in radiographic imaging.

Figure 13A:
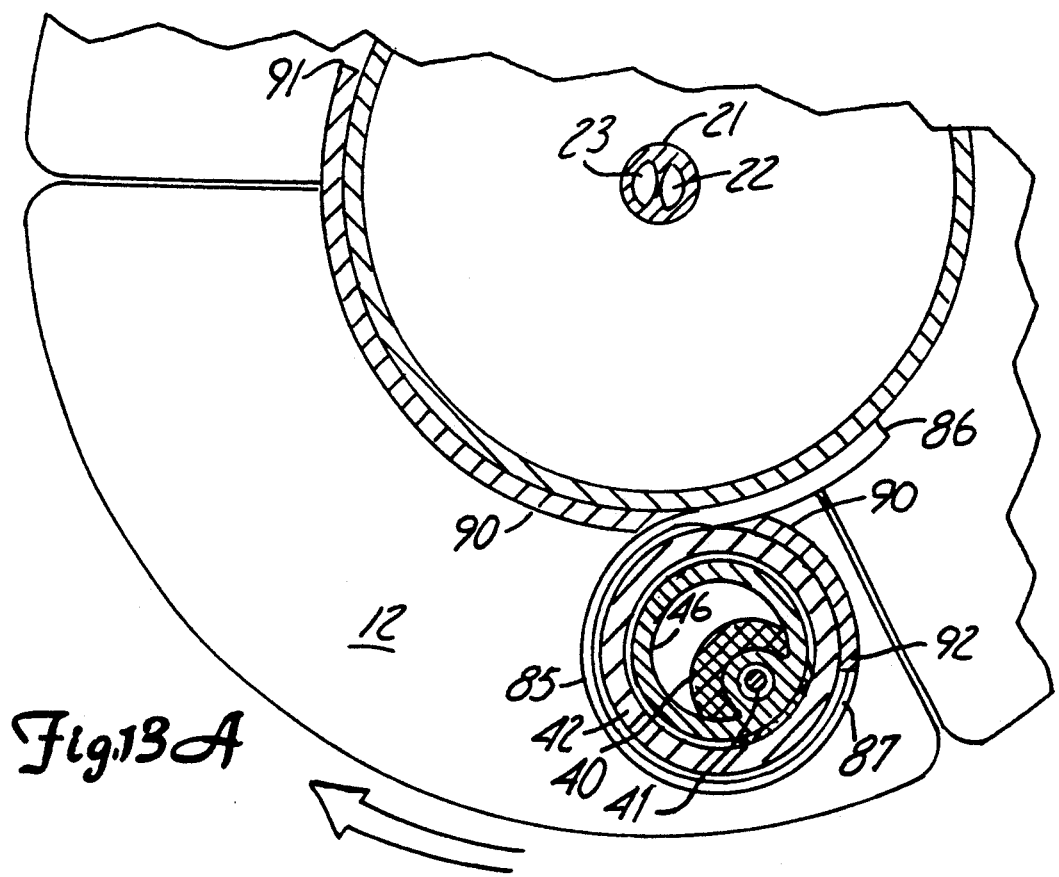
FIG. 13A is a cross-sectional view, partially broken away, of FIG. 13 taken along line 13A—13A thereof.
Figure 13B:
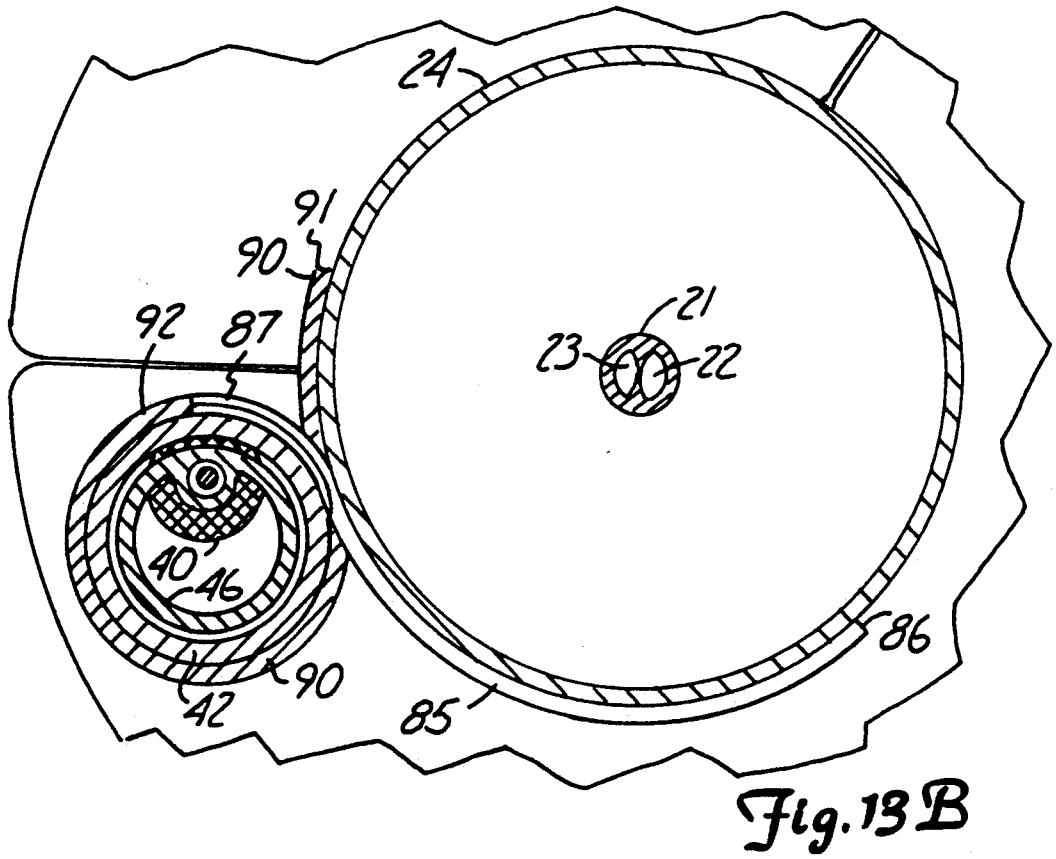
FIG. 13B is a cross-sectional view similar to FIG. 13A shown in a moved position.

FIGS. 13-14 depict an alternate embodiment for providing attachment means to secure the tool 40 with respect to the anchoring balloon 24 and for permitting selected positioning of the deposit removal tool 40 with respect to the anchoring balloon 24. In this embodiment, a set of circumferential straps is provided. In the embodiment illustrated, a set of upper and lower circumferential straps 85 is attached with a first end 86 secured to the anchoring balloon 24 and a second end 87 attached to the guiding catheter 42. A middle strap 90 similarly has a first end 91 attached to the anchoring balloon 24 and a second end 92 attached to the guiding catheter 42. The middle strap 90 is wound about the anchoring balloon 24 in a direction opposite that of the upper and lower straps 85. The guiding catheter 42 may then be rotated to move it circumferentially about the anchoring balloon 24. Referring to FIGS. 13A-13B, as the guiding catheter is rotated clockwise, the middle strap 90 will wind up on the guiding catheter 42, while the upper and lower straps 85 will unwind from the guiding catheter 42; as this occurs, the guiding catheter 42 will move clockwise about the anchoring balloon 24 from the position illustrated in FIG. 13A to the position illustrated in FIG. 13B. FIG. 14 shows a slightly modified arrangement of this embodiment where the straps 85 and 90 are somewhat longer, permitting movement of the guiding catheter 42 substantially entirely around the anchoring balloon 24.

Figures 15, 15A:
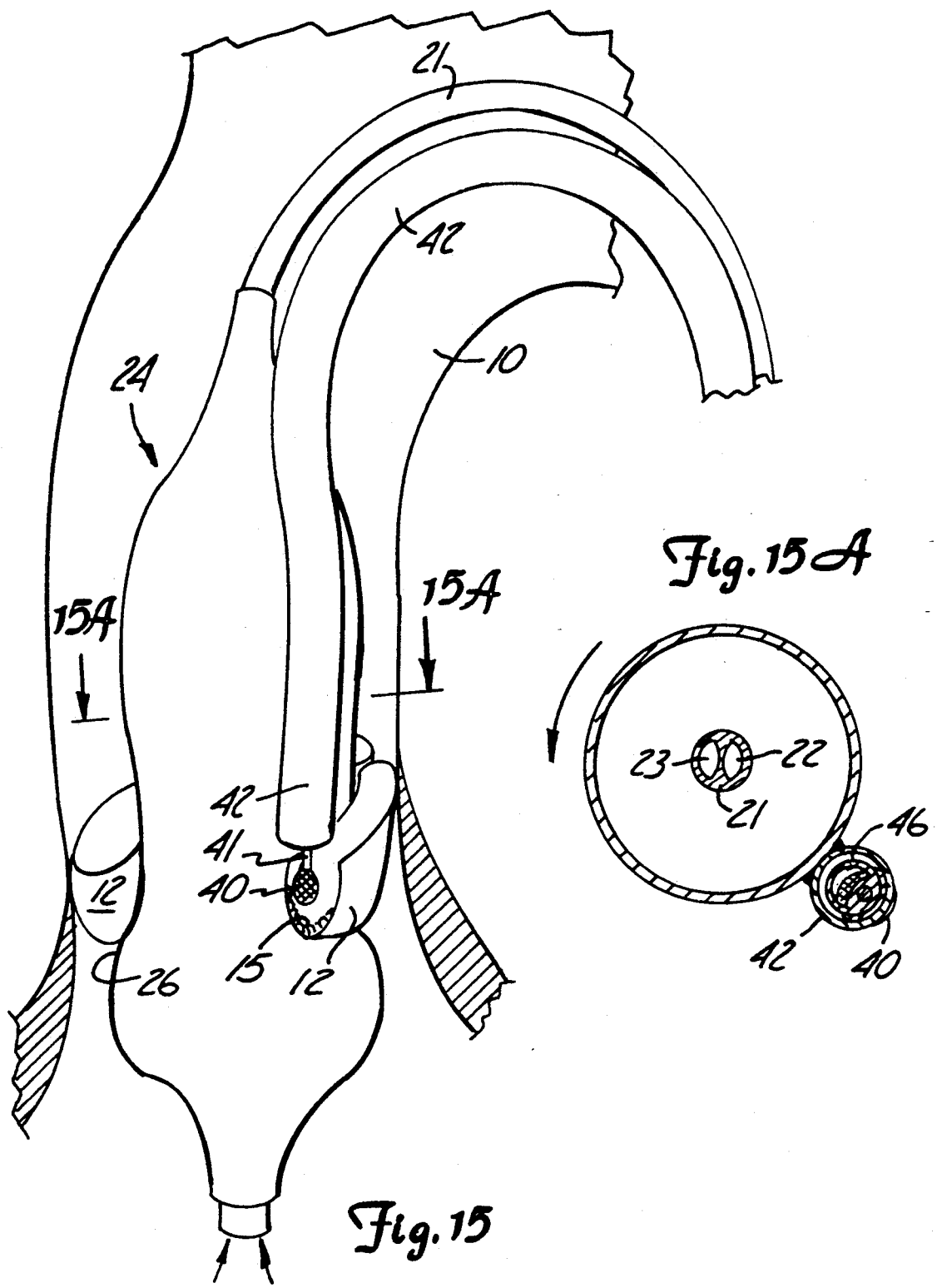
FIG. 15 is a modified embodiment of the invention.
FIG. 15A is a cross-sectional view of FIG. 15, taken along line 15A—15A thereof.

FIGS. 15 and 15A show another simplified embodiment of the invention. In this embodiment guiding catheter 42 is attached directly to the wall of the anchoring balloon 24. Positioning of the tool is accomplished merely by rotating the anchoring balloon 24 itself with respect to the aortic valve, and by rotating the positioning catheter 46 within the guiding catheter 42.

Figures 16, 16A:
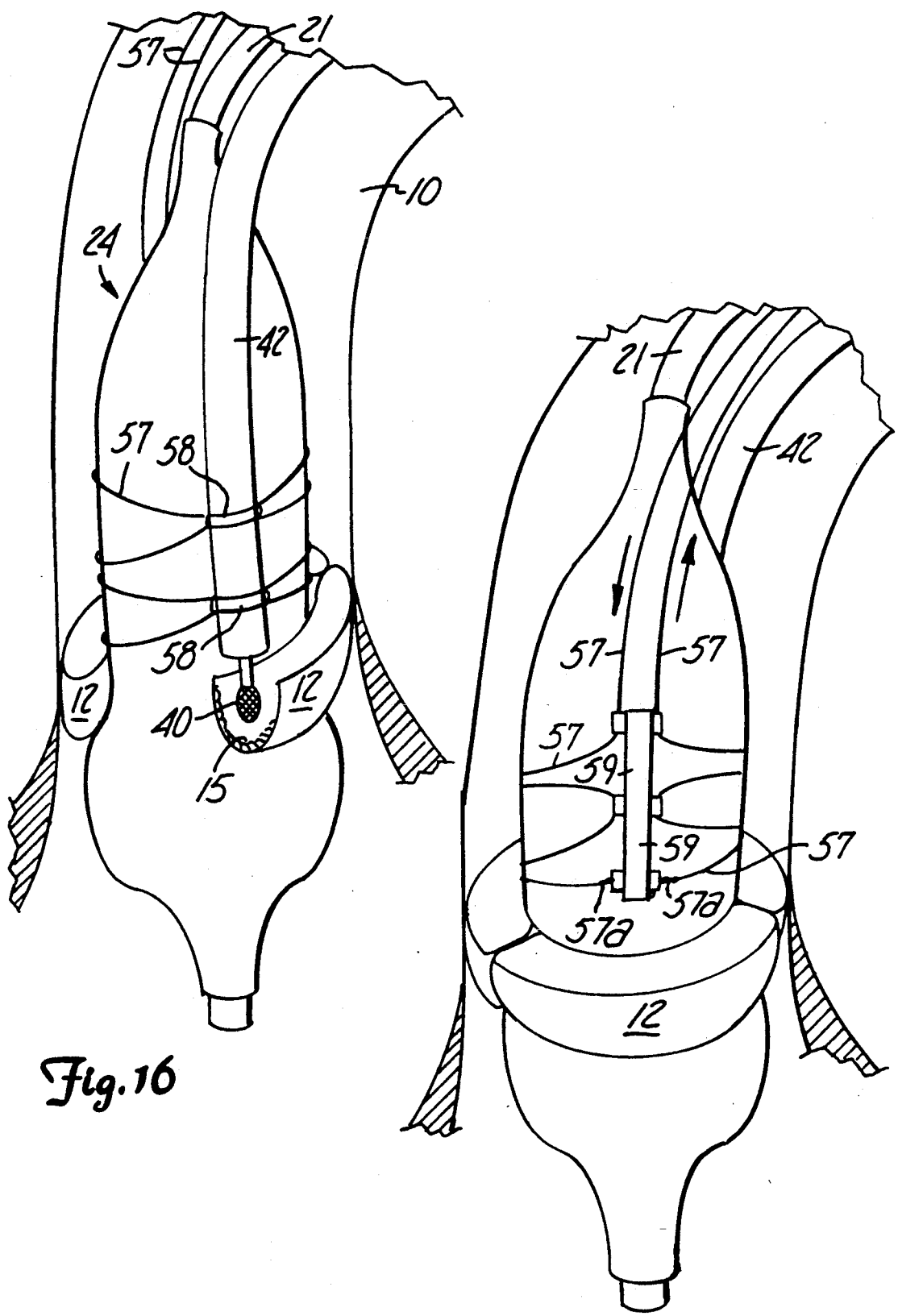
FIG. 16 is yet another modified embodiment of the invention
FIG. 16A is a view of the other side of the embodiment shown in FIG. 16.

FIGS. 16-16A show yet another embodiment for controllably positioning the guiding catheter with respect to the anchoring balloon (FIG. 16A showing the back side of FIG. 16). In this embodiment a pair of cords 57 can be manipulated to move the guiding catheter 42 about the periphery of the anchoring balloon 24. Each cord 57 is attached at its distal end 57a to a pulley strip 59 that in turn is attached to the anchoring balloon (FIG. 16A). The cord is then threaded through a series of pulleys on a pair of pulley rings 58 carried by the guiding catheter 42 and pulleys on the fixed pulley strip 59. By pulling on one of the cords 57 while releasing the other the guiding catheter will be pulled around the anchoring balloon in one direction; by pulling on the other cord, the guiding catheter will be pulled around in the other direction.

In practice, the decalcification procedure of the invention proceeds as follows. Access to the aorta 10 is obtained, typically through percutaneous or cut down entry into the femoral artery with a guide wire. The guide wire is advanced through the femoral and iliac arteries and the aorta to the aortic valve and then across the aortic valve into the left ventricle (L.V.). A deflated anchoring balloon catheter 24 is then advanced over the guide wire to a position across the aortic valve with the distal tip of the balloon in the left ventricle (L.V.). The anchoring balloon 24 is then inflated and slightly retracted to engage the shoulder 26 of the anchoring balloon 24 against the inferior surface of the calcified valve leaflets 12. (Depending on the situation and the type of anchoring balloon catheter utilized, cardiopulmonary support/bypass may be necessary once the balloon is inflated, and this can be accomplished as described below.)

When utilizing the embodiment having the collapsable guiding catheter sheath 44 attached to the anchoring balloon 24, the guiding catheter 42 may then advanced through the sheath 44 to proper position adjacent the anchoring balloon 24. The deposit removal tool 40, together with the positioning catheter 46, may then be advanced through the guiding catheter 42 to their proper positions. One or both of the positioning balloons 70, 76, may then be inflated to circumferentially locate the guiding catheter 42 and, hence, the deposit removal tool 40 as desired. The positioning catheter may also be rotated to further position the removal tool 40. The tool 40 in turn may also be slightly advanced or withdrawn as necessary. Operation of the removal tool 40 can then be commenced, with blood and dislodged calcification deposits being sucked up through the main lumen 50 of the positioning catheter 46. When deposits from a particular leaflet 12 have been removed, the anchoring balloon 24 can be deflated partially and rotated to position the removal tool 40 adjacent one of the other leaflets 12. When the calcification deposits have been removed, the entire device may be removed essentially by reversing the process of inserting the device.

During the procedure, conventional radiographic imaging techniques may be utilized to allow the physician to view the relative locations of the anchoring balloon 24, deposit removal tool 40, and the calcified deposits which are to be removed from the aortic valve leaflets. Preferably, the components of the anchoring balloon and removal tool and associated catheters are either radio opaque or marked with radio opaque markers so that they will be visible by conventional radiographic imaging techniques. Visualization of the anchoring balloon and positioning balloons and the inferior surface of the leaflets in contact with the anchoring balloon 24 is further facilitated by using radiographic contrast solution for inflation of the balloons 24, 70 and 76. Contrast may also be injected either through the lumen 22 of the anchoring balloon 24, or through the main lumen 50 of the positioning catheter 46.

In addition, known ultrasound imaging techniques may also be utilized. N. Bom and J. Roelandt have edited a reference book entitled "Intravascular Ultrasound," (Kluwer Academic Publishers 1989), containing a variety of articles detailing techniques, developments, and clinical perspectives on intravascular ultrasound procedures. FIG. 17 illustrates one possible embodiment utilizing a phased array ultrasound transducer 29 (containing many small acoustic elements 128) mounted on the catheter 21 of the anchoring balloon 24. This transducer 29 will generate a cross-sectional view of the aortic valve and the location of the calcified deposits to be removed. The details of such ultrasound techniques for intravascular imaging are well-known, as described in the above-mentioned text. Ultrasound preferably is used in conjunction with and not to the exclusion of conventional radiographic imaging.

Figure 18:
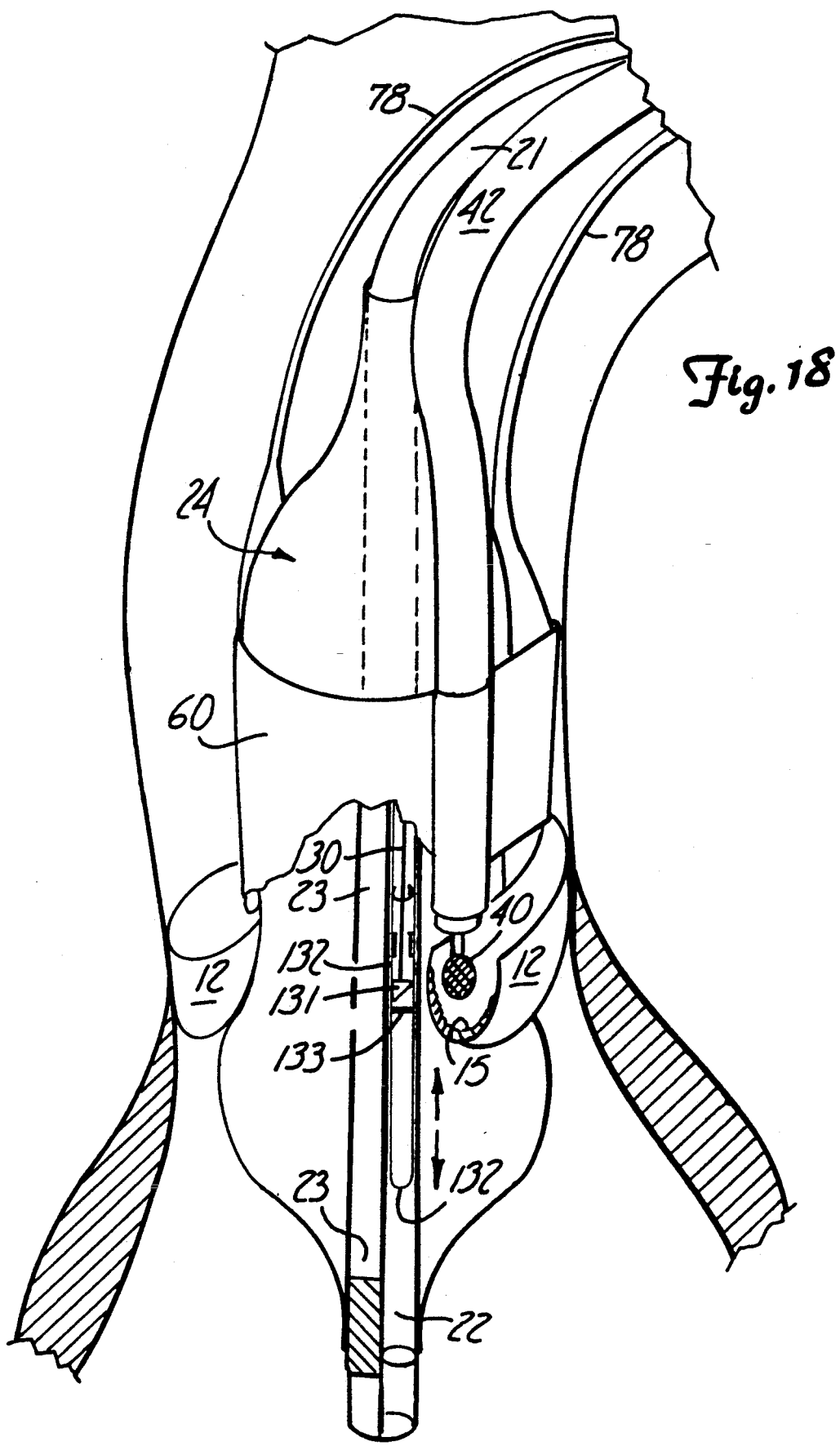
FIG. 18 is a perspective, partially broken-away view of a yet one more embodiment of the invention.

FIG. 18 shows another embodiment of the invention where an ultrasound catheter 132 is positioned inside one of the lumens of the catheter 21 of the anchoring balloon 24, preferably the lumen 22. The ultrasound catheter 132 shown in FIG. 18 operates on a principle different from the one shown in FIG. 17. Instead of a phased array transducer, the ultrasound catheter 132 includes an echo transducer 133 and a mirror 31 rotated by a flexible shaft 30. This embodiment is advantageous in that it allows the ultrasound catheter 132 to be advanced or retracted in the lumen 22 of the anchoring balloon 24 to provide a cross-sectional image at the desired more distal or more proximal position. As these types of ultrasound catheters and procedures are described in greater detail in the Bom reference identified above, further description is not necessary here.

During performance of the decalcification procedure, it is desirable to provide cardiopulmonary support/bypass for the patient, as an anchoring balloon 24 of the type depicted in FIG. 1 substantially occludes the aortic valve. FIGS. 19-23 depict several variations for providing such support.

Figure 19:
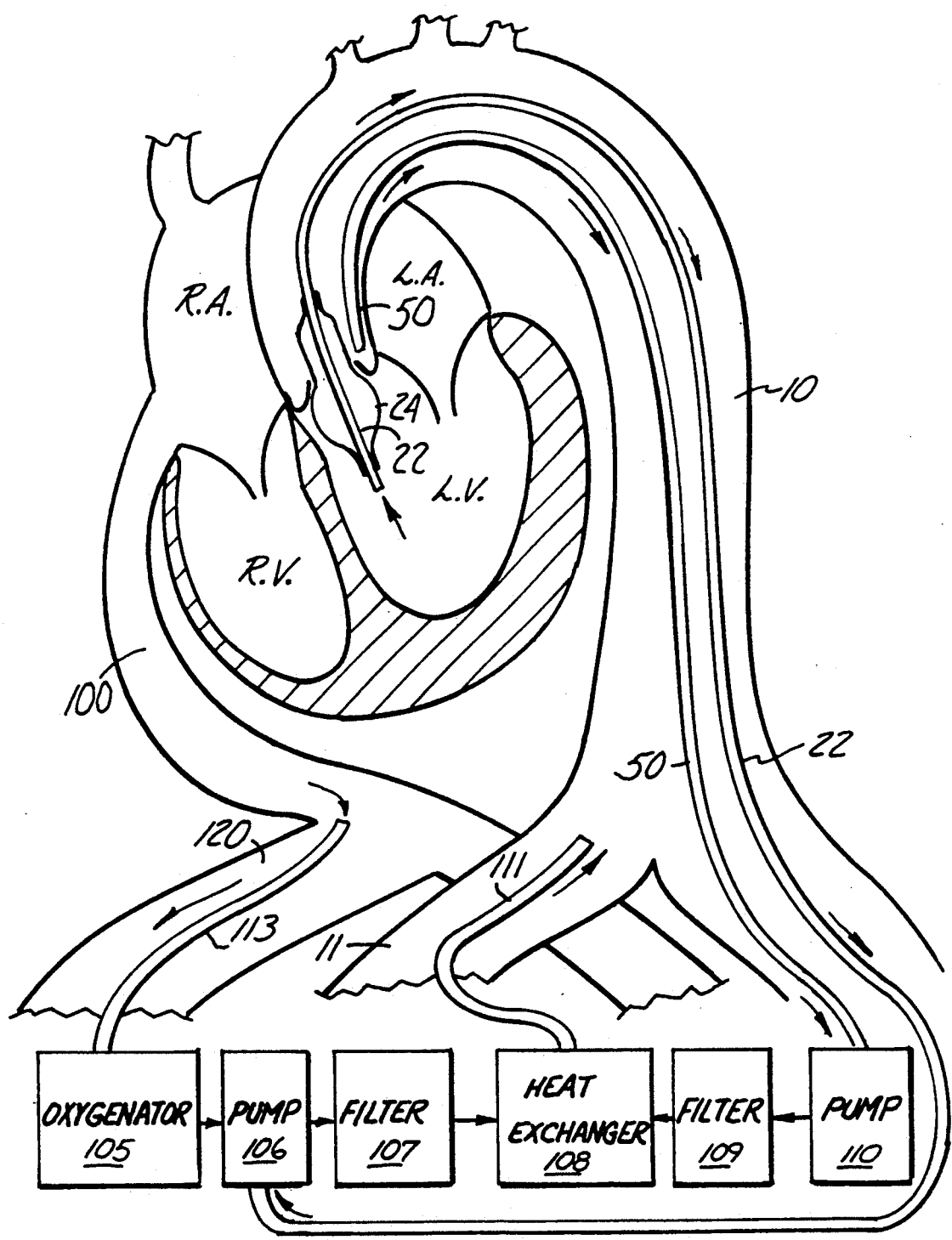
FIG. 19 is a schematic illustration of a cardiopulmonary support/bypass system utilized in conjunction with the decalcification apparatus of the invention.

FIG. 19 depicts in schematic form a first variation. Blood is ejected/withdrawn from the left ventricle through the central lumen 22 of the anchoring balloon catheter 24 and delivered to a first pump 106. That pump 106 in turn delivers the blood through a filter 107 to a heat exchanger 108 and then through percutaneous catheter 111 back to the iliac artery 11 and the aorta 10. Blood and calcification deposit debris loosened by the removal tool 40 are aspirated into the main lumen 50 of the positioning catheter containing the tool shaft by a second pump 110. Debris is filtered out by a second filter 109, after which the blood is sent through the heat exchanger 108 and the return catheter 111 back to the aorta 10.

To assure adequate extracorporeal circulation an additional blood withdrawal catheter 113 is percutaneously introduced into the iliac vein 120. Blood withdrawn through this catheter 113 should be oxygenated before being returned to the body. This may be accomplished by a conventional oxygenator 105 which in turn passes the blood through pump 106 to filter 107, and heat exchanger 108, whereupon the blood may be returned to the aorta 10 through the return catheter 111.

Figure 20:
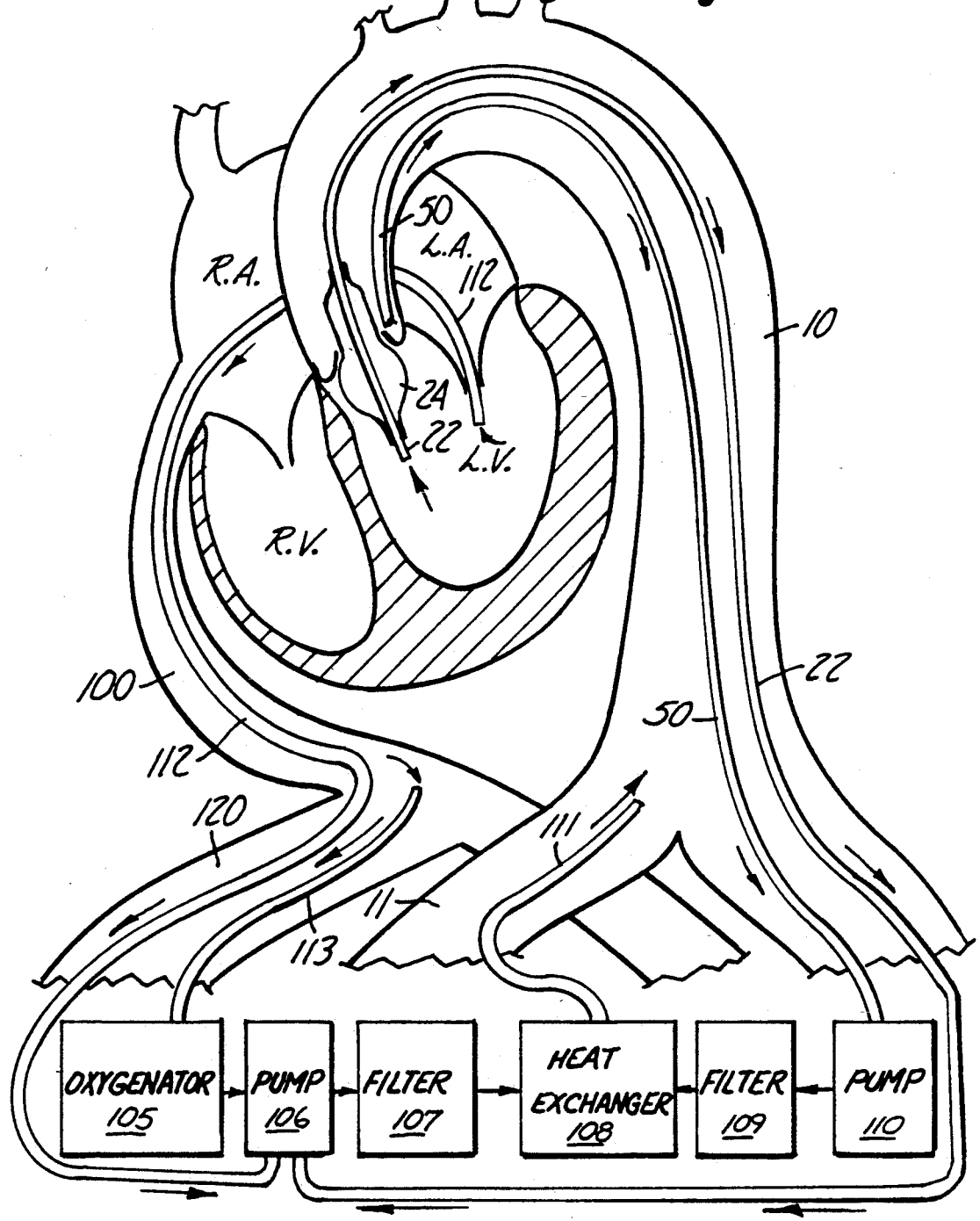
FIG. 20 shows a modified arrangement of the cardiopulmonary support system of FIG. 19.

In order to maintain blood flow through the heart sufficient to significantly reduce the risk of cardiac asystole, particularly in light of the relatively small size of the central lumen 22 of the anchoring balloon catheter 24, a supplemental catheter 112 may be advanced percutaneously through the vena cava 100 to the left ventricle (L.V.) by way of the right atrium (R.A.) and the left atrium (L.A.), as shown in FIG. 20. To achieve this positioning of the catheter 112, the catheter must pass through the thin septum between the right atrium (R.A.) and left atrium (L.A.), such as is commonly done in mitral balloon valvuloplasty (see, e.g., T. Bashore, "Invasive Cardiology Principles and Techniques" (B.C. Decker Inc.) at pp. 147ff). This catheter 112 may be of substantial diameter in comparison to the central lumen 22 of the anchoring balloon catheter 24. Blood ejected/withdrawn through this catheter 112 passes from pump 106 through filter 107 to heat exchanger 108 and then through the return catheter 111 back to the aorta 10. Catheters 112 and 113 may be arranged in a double lumen catheter, which may be a side by side double lumen, a coaxial double lumen, or even a single lumen catheter that has holes in a wall thereof in an intermediate portion, defining the distal "end" of the vein access catheter 113.

The foregoing blood paths through the lumen 22 of the anchoring catheter 24 and through catheter 112 usually will allow sufficient cardiac output to prevent cardiac asystole.

Figure 21:
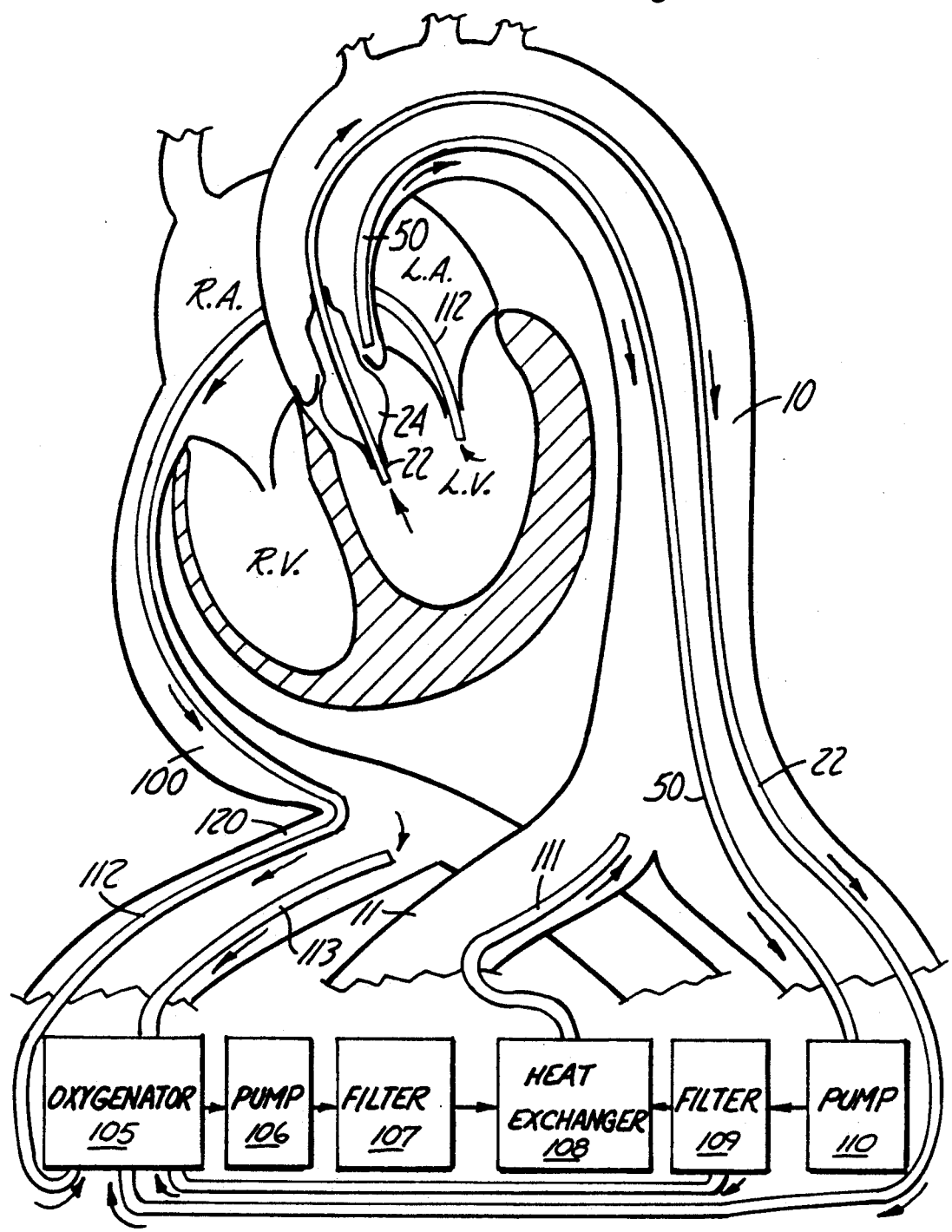
FIG. 21 shows a modified arrangement of the cardiopulmonary support system of FIG. 19.
Figure 22:
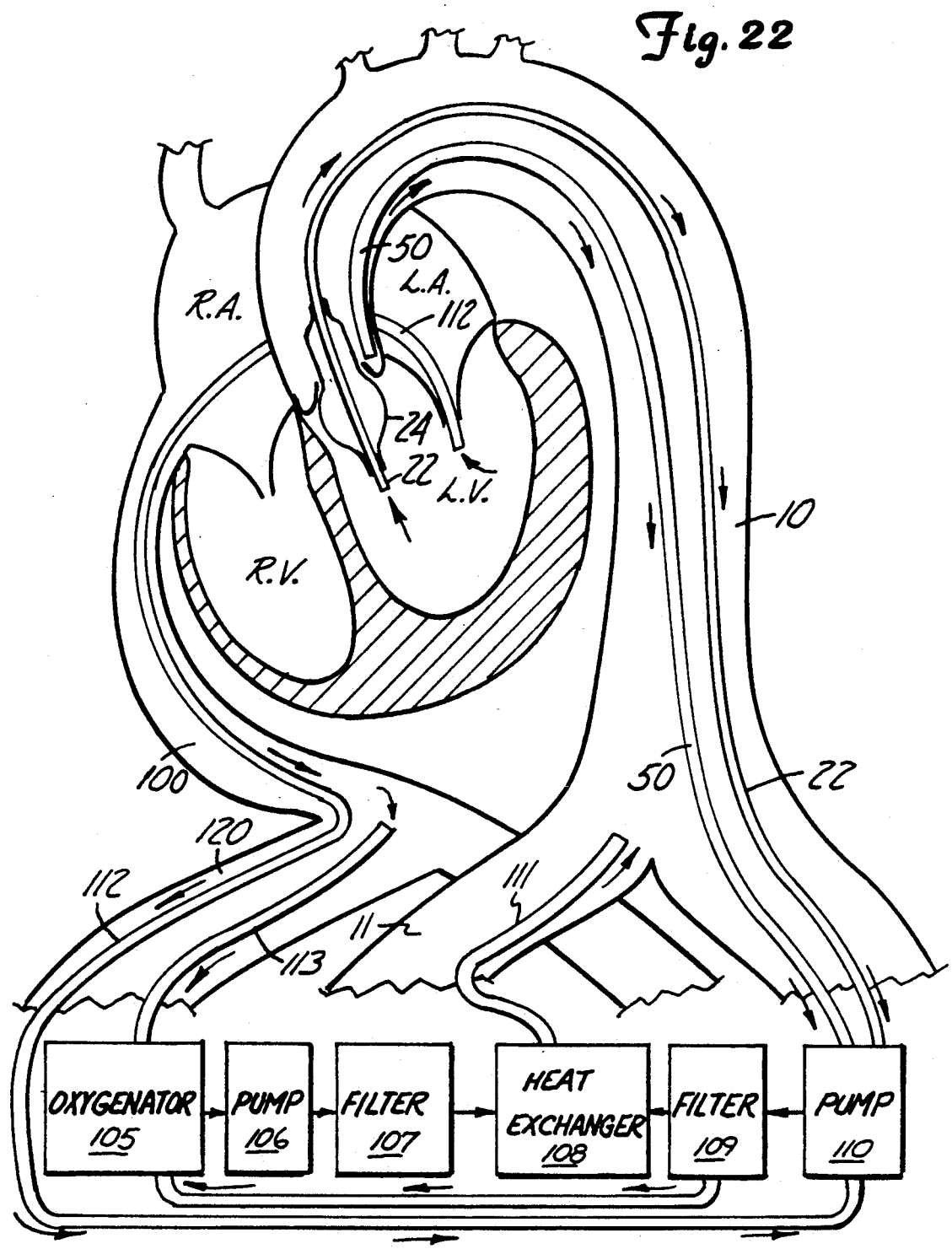
FIG. 22 shows a modified arrangement of the cardiopulmonary support system of FIG. 19.

FIG. 21 depicts an alternate arrangement for external blood flow. In this configuration, the blood withdrawn from the left ventricle of the heart (through the larger catheter 112 and through the central lumen 22 of the anchoring balloon catheter 24) is passed directly to the oxygenator 105 before being returned (via pump 106, filter 107 and heat exchanger 108) to the aorta 10 through return catheter 111. In yet another configuration shown in FIG. 22, all of the blood withdrawn from the heart is first passed through pump 110 and the second filter 109 before being sent to the oxygenator 105.

Figure 23:
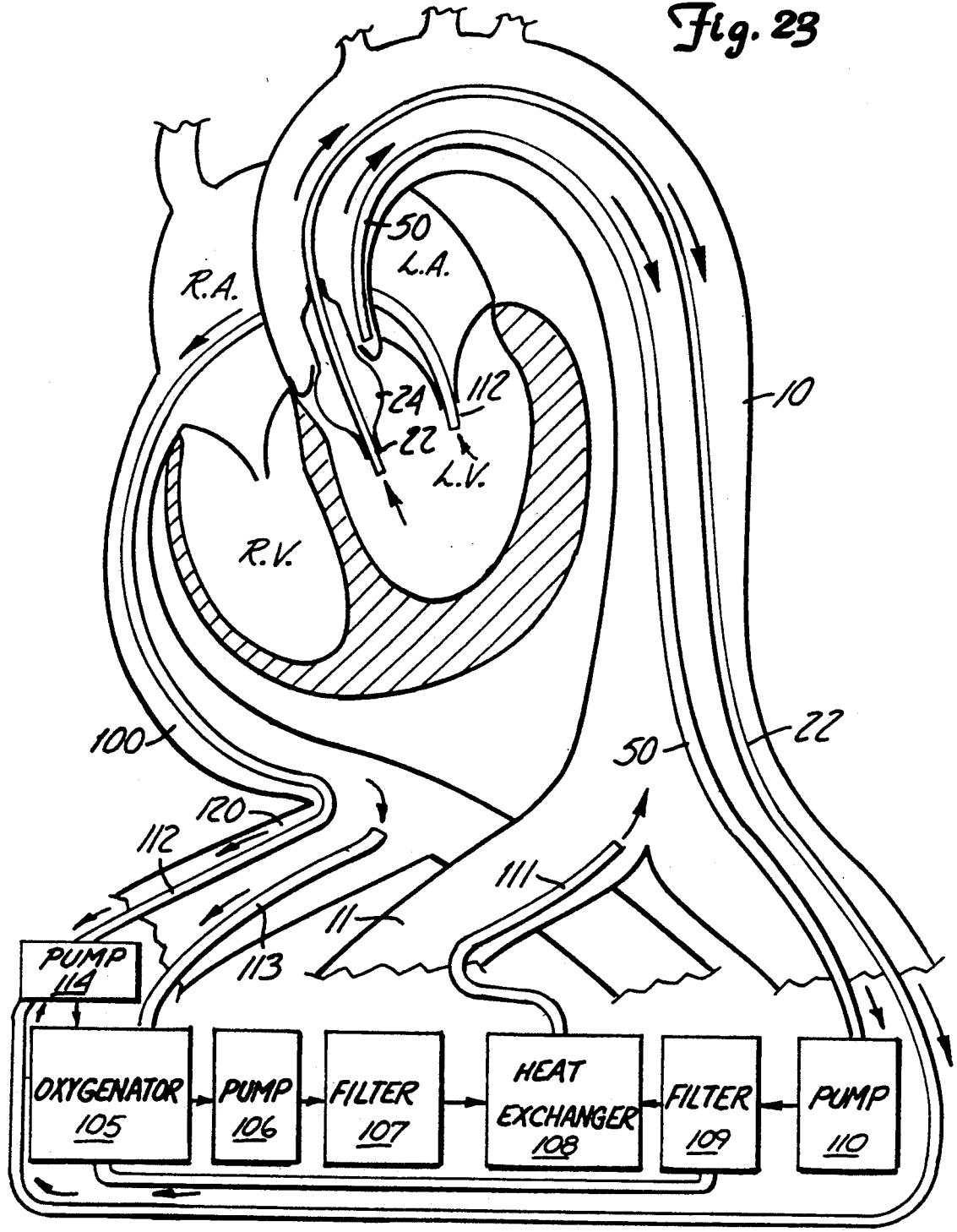
FIG. 23 shows a modified arrangement of the cardiopulmonary support system of FIG. 19.

In yet a further embodiment shown in FIG. 23, an additional pump 114 is provided upstream from the oxygenator but separate from the second pump 110, thereby permitting separate control of the blood withdrawn by the main lumen 50 of the catheter containing the deposit removal tool. Other equivalent arrangements may also be utilized. The arrangements depicted in FIGS. 19-23 demonstrate, however, that cardiac function and coronary circulation can be maintained even while the decalcification procedure is being performed. Rapid cardiac pacing at about 180-200 beats per minute also may be employed to lower cardiac output, particularly when the trans-septal approach to the left ventricle (L.V.) is not used.

Figure 24:
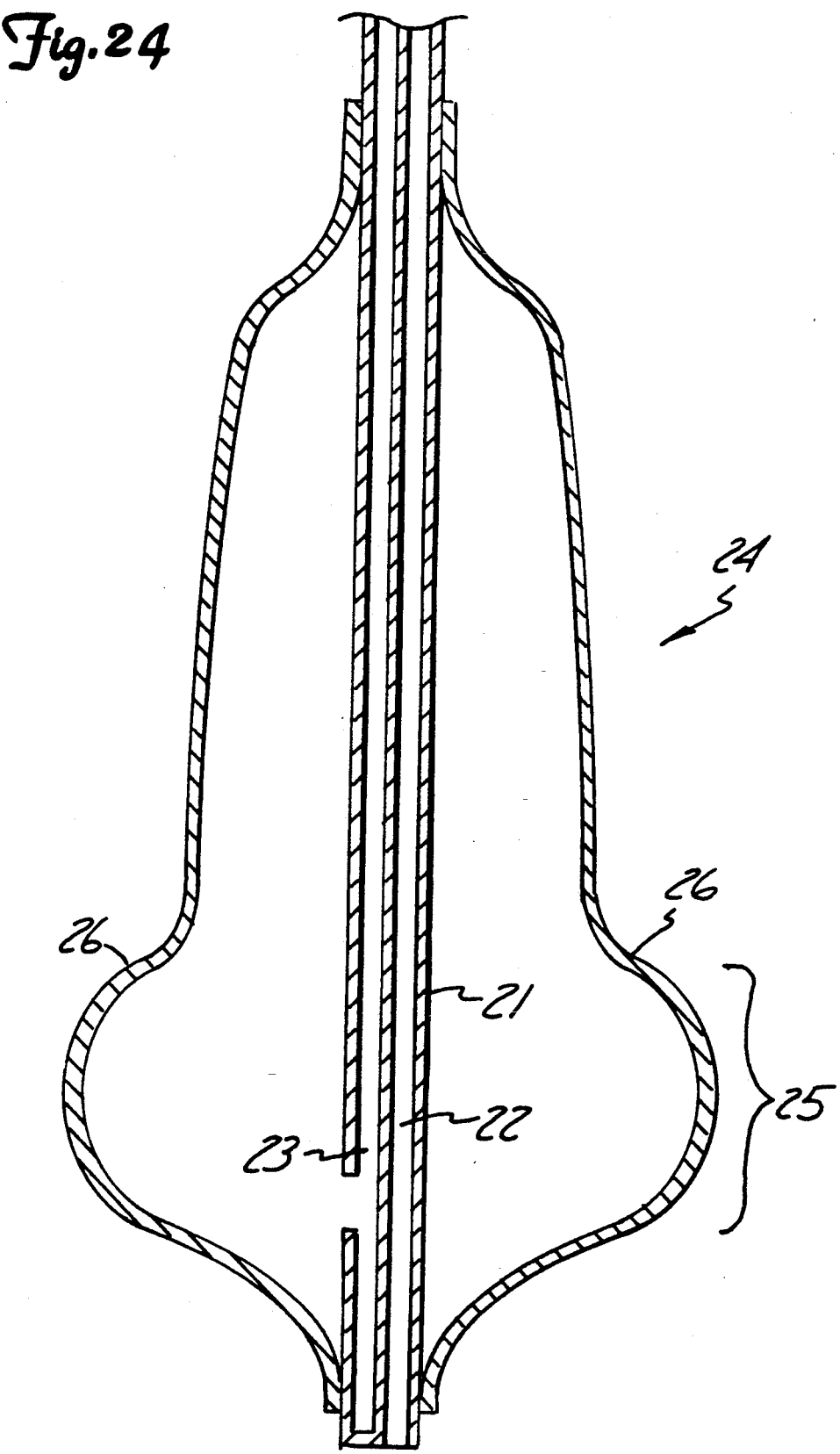
FIG. 24 is a cross-sectional view of an anchoring balloon of the invention.

FIGS. 24-26A depict possible configurations for the anchoring balloon of the invention. FIG. 24 shows in cross section the anchoring balloon depicted in FIG. 1 and many of the other figures. The balloon includes a distal portion 25 that is of a larger diameter than the rest of the balloon, thereby providing a shoulder 26 for engaging and supporting the inferior surface of the valve leaflets 12—the balloon is inserted pas the leaflets 12 and then inflated as it is withdrawn to allow the shoulder 26 to seat against the inferior surface of the valve leaflets 12.

Figure 25:
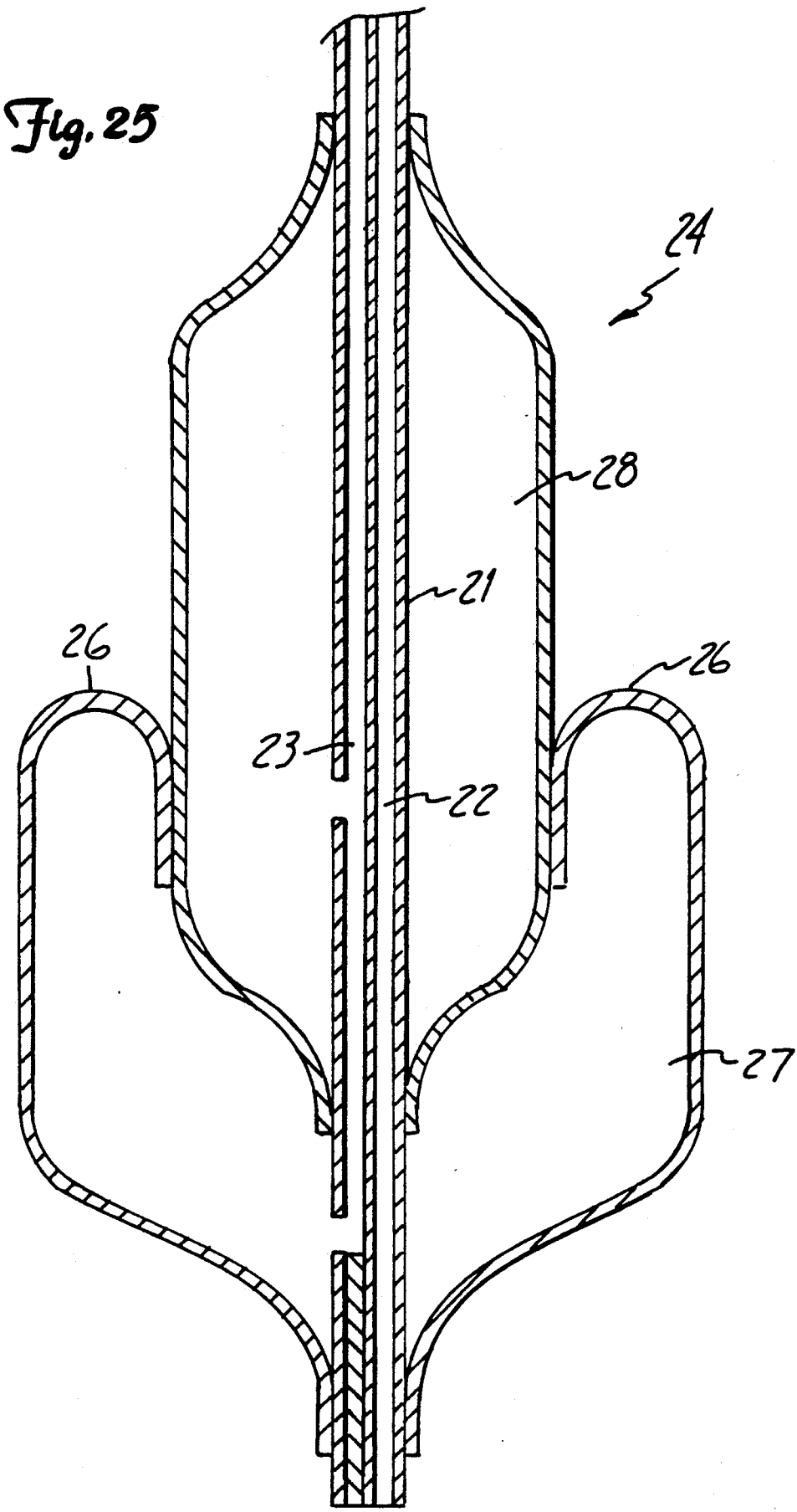
FIG. 25 is a cross-sectional view of a modified embodiment of the anchoring balloon of the invention.
Figure 26:
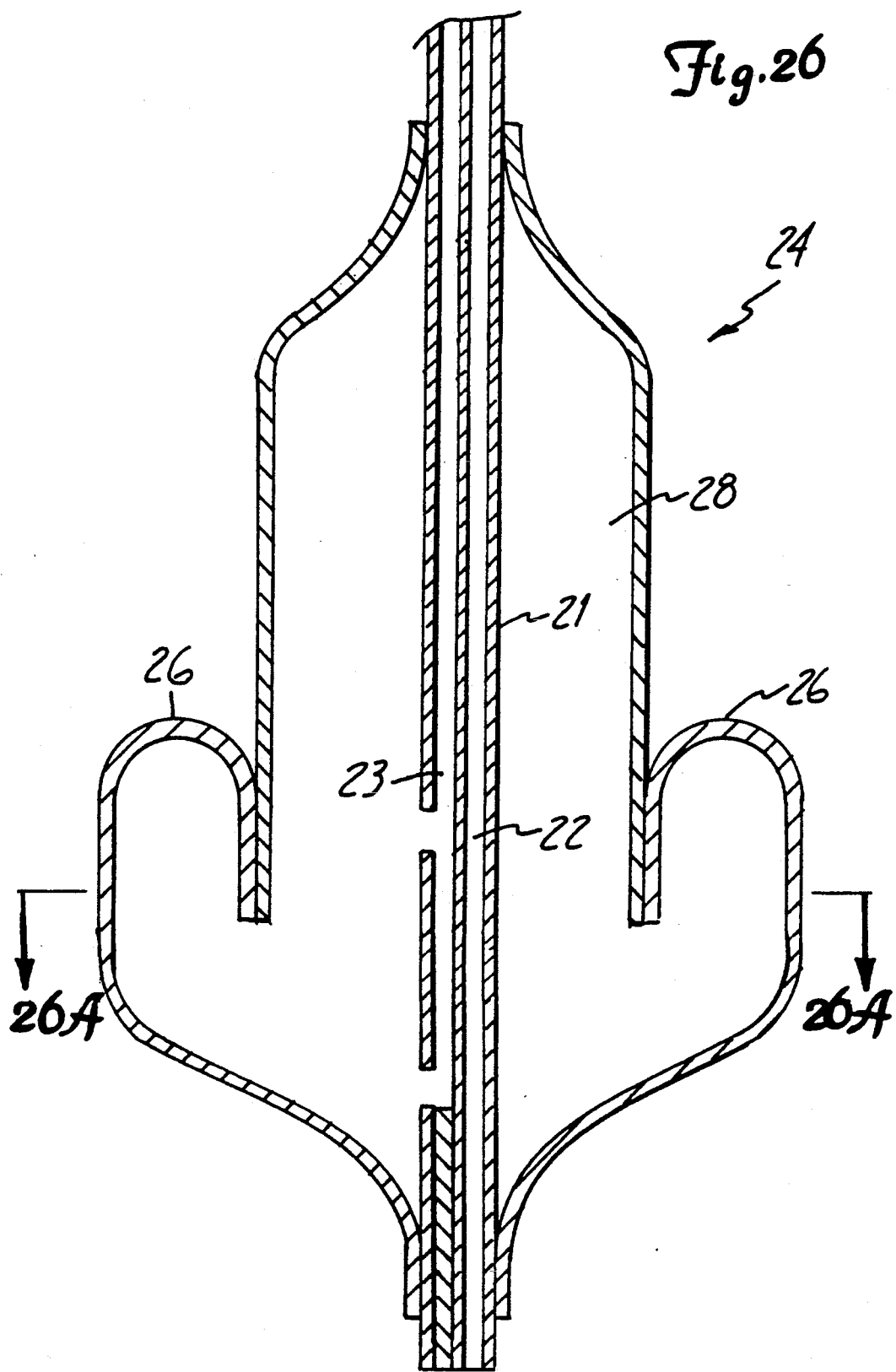
FIG. 26 is a cross-sectional view of another modified embodiment of an anchoring balloon of the invention.
Figure 26A:
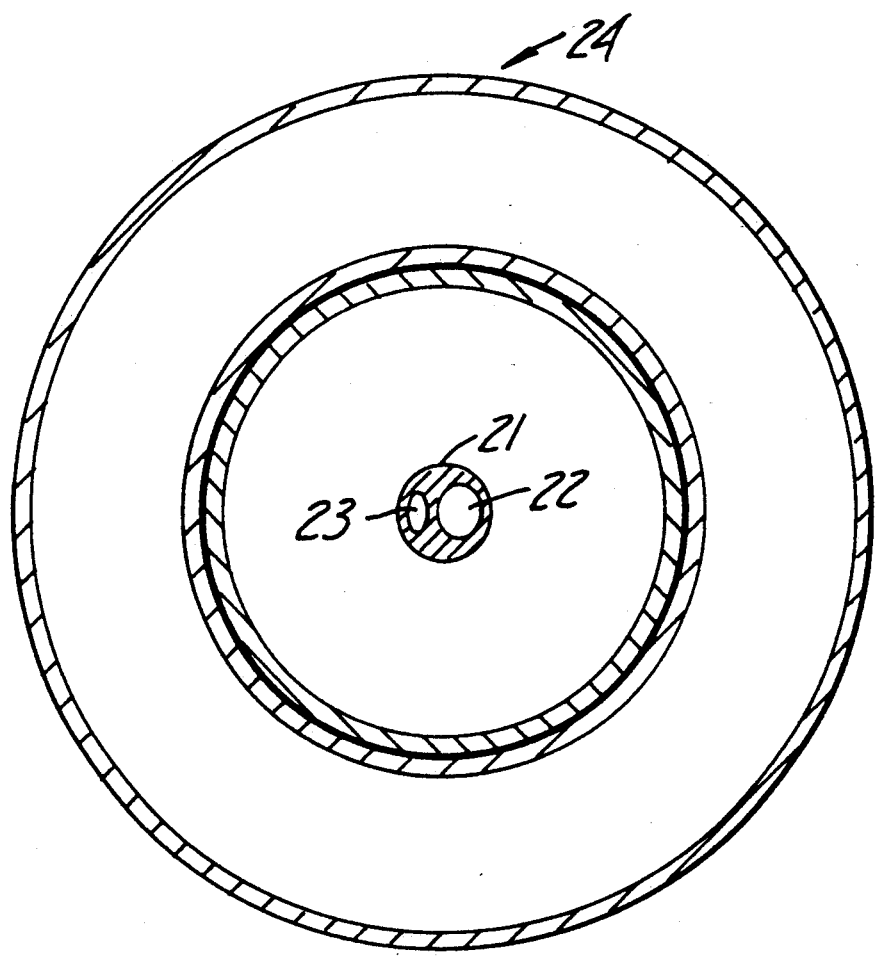
FIG. 26A is a cross-sectional view of FIG. 26, taken along line 26A—26A thereof.

In FIG. 25 the anchoring balloon 24 includes an enhanced shoulder 26 formed by constructing a distal chamber 27 which is in fluid communication with the main chamber 28. The enhanced shoulder 26 provides an even more secure engagement against the inferior surface of the valve leaflets 12. FIG. 26 shows a modified version of the balloon of FIG. 25 wherein the main chamber is merged with the distal chamber, but the enhanced shoulder 26 is preserved. FIG. 26A shows a cross-section of the anchoring balloon catheter 24 with the catheter 21 having two lumens, the lumen 22 through which a guide wire may be advanced or withdrawn and through which fluid may be withdrawn or injected, and the lumen 23 which communicates with the interior of the balloon to inflate and deflate it. Any of the embodiments of FIGS. 24-26A can be modified so that the shoulder portion is manufactured from a thin layer of stretchable material (such as silicone) and the remaining portion of the balloon from a substantially non-stretchable material (or a stretchable material that is reinforced so that it will not stretch beyond a certain point). With this construction, the balloon can be controllably inflated so that the thin, stretchable shoulder portion 26, which engages and supports the leaflets 12 of the aortic valve, will conform very closely to the shape of the leaflet, giving close, uniform support to the leaflet.

Figure 27A:
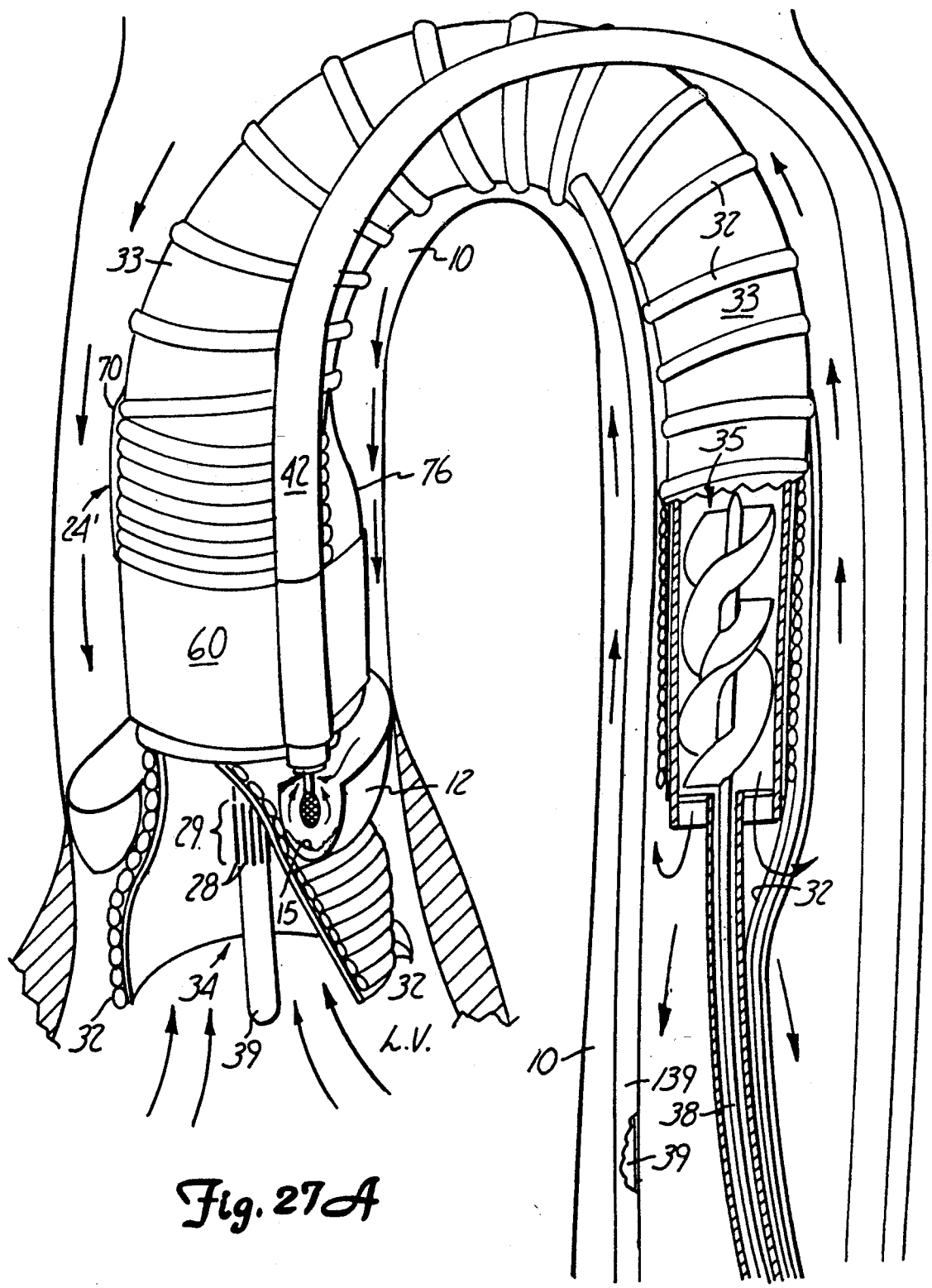
FIG. 27A is a perspective, broken-away view in partial cross-section showing yet another embodiment of the apparatus of the invention.
Figure 27B:
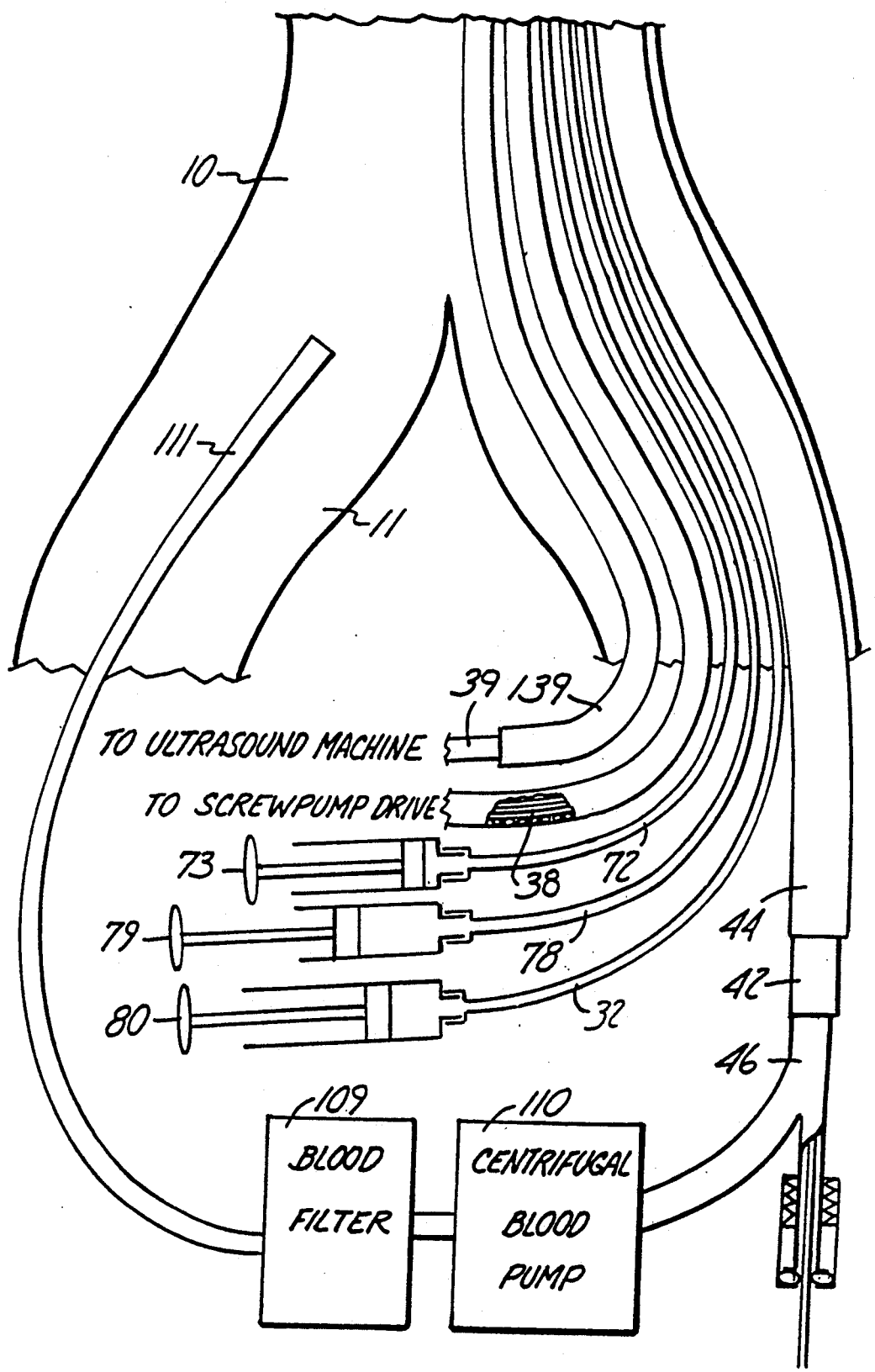
FIG. 27B shows the proximal ends of the various catheters utilized in the embodiment of FIG. 27A.
Figure 28:
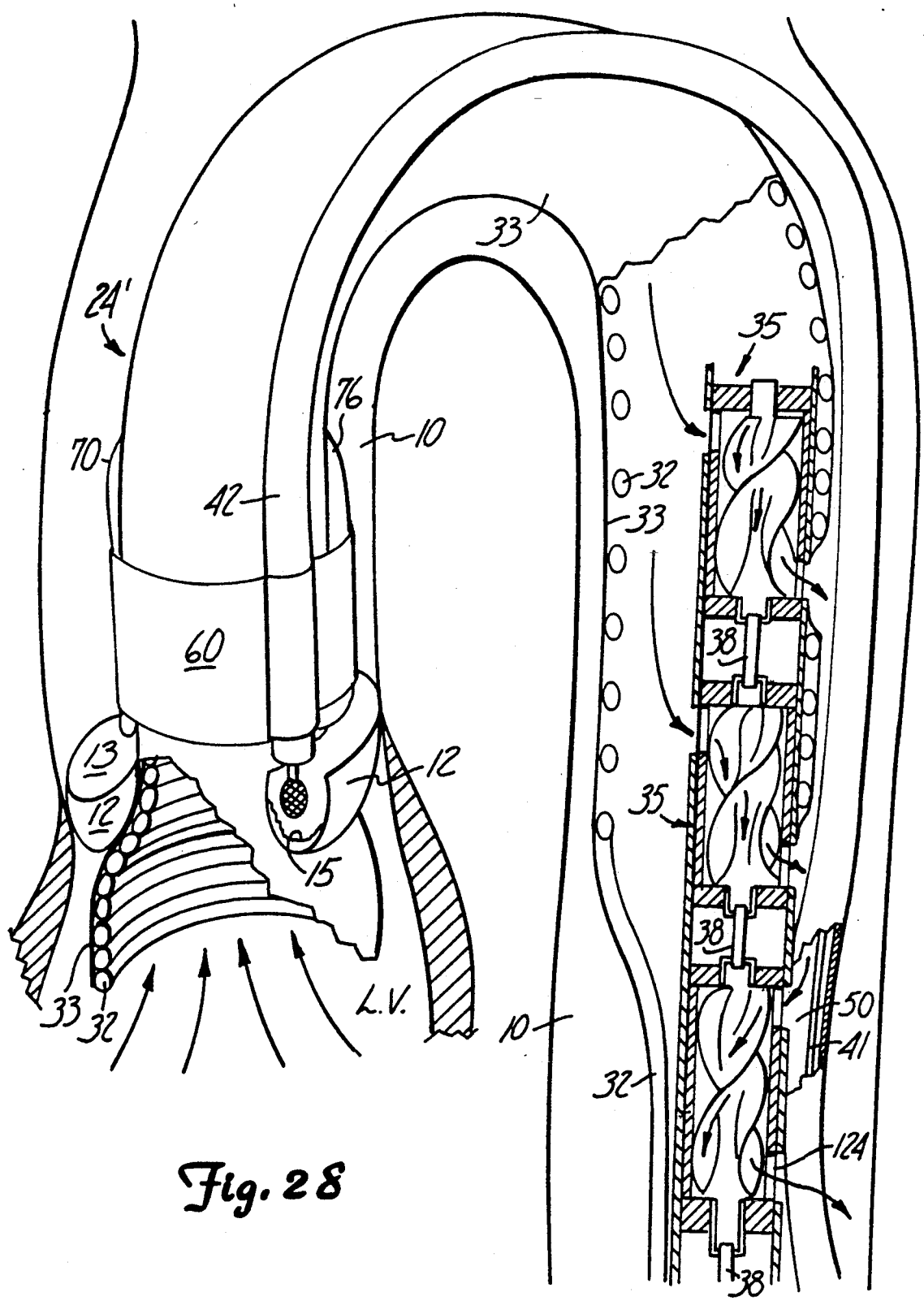
FIG. 28 shows a modified version of the embodiment of FIG. 27A.

FIGS. 27A-30 depict an alternate embodiment of the invention that may partially or entirely eliminate the need for the cardiopulmonary support/bypass system depicted in FIGS. 19-23. In this embodiment, the anchoring balloon 24' consists of an inflatable tube 32 coiled into a helical configuration and held in this helical configuration by an inner sheath or skin 33, defining a large bore lumen 34. The helical anchoring balloon 24' allows its large bore lumen 34 to present a substantially open passageway distally and proximally, allowing blood to continue flowing through the balloon even when it is inflated and holding the valve leaflets 12 in position for the decalcification procedure. If desired, a rotating screw-type pump 35 may be secured in the proximal portion of the balloon to maintain circulation through the aorta 10 while the procedure is being performed. Such screw-type pumps are well known, such as the HEMOPUMP® brand pump available through Johnson & Johnson. (FIG. 28 shows that multiple screw pumps may be used in parallel to increase the volume of blood pumped. FIG. 28 also shows that one of the screw pumps—e.g., the proximal one—may be used to pump blood from the main lumen 50 of the positioning catheter through the filter 124 at the proximal end of such screw pump.)

A catheter 39 (FIG. 27A) is disposed in the central portion of the distal end of the helical anchoring balloon 24'. The catheter 39 is carrying the phased array ultrasound transducers 29, described previously. The ultrasound catheter 39 desirably exits the large bore lumen 34 through the skin 33 intermediate of the position of the screw pump 35 and the distal end of the helical anchoring balloon 24'. To allow assembly of the catheter into the helical anchoring balloon 24' after insertion of the balloon into the patient, a flaccid sheath 139 may be attached to the skin 33 at the point of entry of the catheter into the large bore lumen 34. Thus, the deflated, furled balloon may be first inserted; once in position, it can be inflated, and the catheter 39 can then be inserted through the flaccid sheath 139 to its position as shown in FIG. 27A. A guide wire 136 may also be advanced via the flaccid sheath 139 or via the lumen of the catheter 39 as necessary.

FIG. 27B shows the proximal end of the various catheters and lumens attached to the configuration in FIG. 27A, including the catheter 39 (containing leads for the ultrasound transducer 29), the drive shaft 38 for the screw pump 35, a syringe (or similar inflation device) 80 connected to the proximal end of tube 32 for inflating the anchoring balloon, inflation devices 73 and 79, respectively, for the first and second positioning balloons, a blood pump 110 for withdrawing blood through the main lumen 50 of the positioning catheter 46, a blood filter 109 and a return catheter 111 to return filtered blood back to an artery (usually the aorta).

Figure 29:
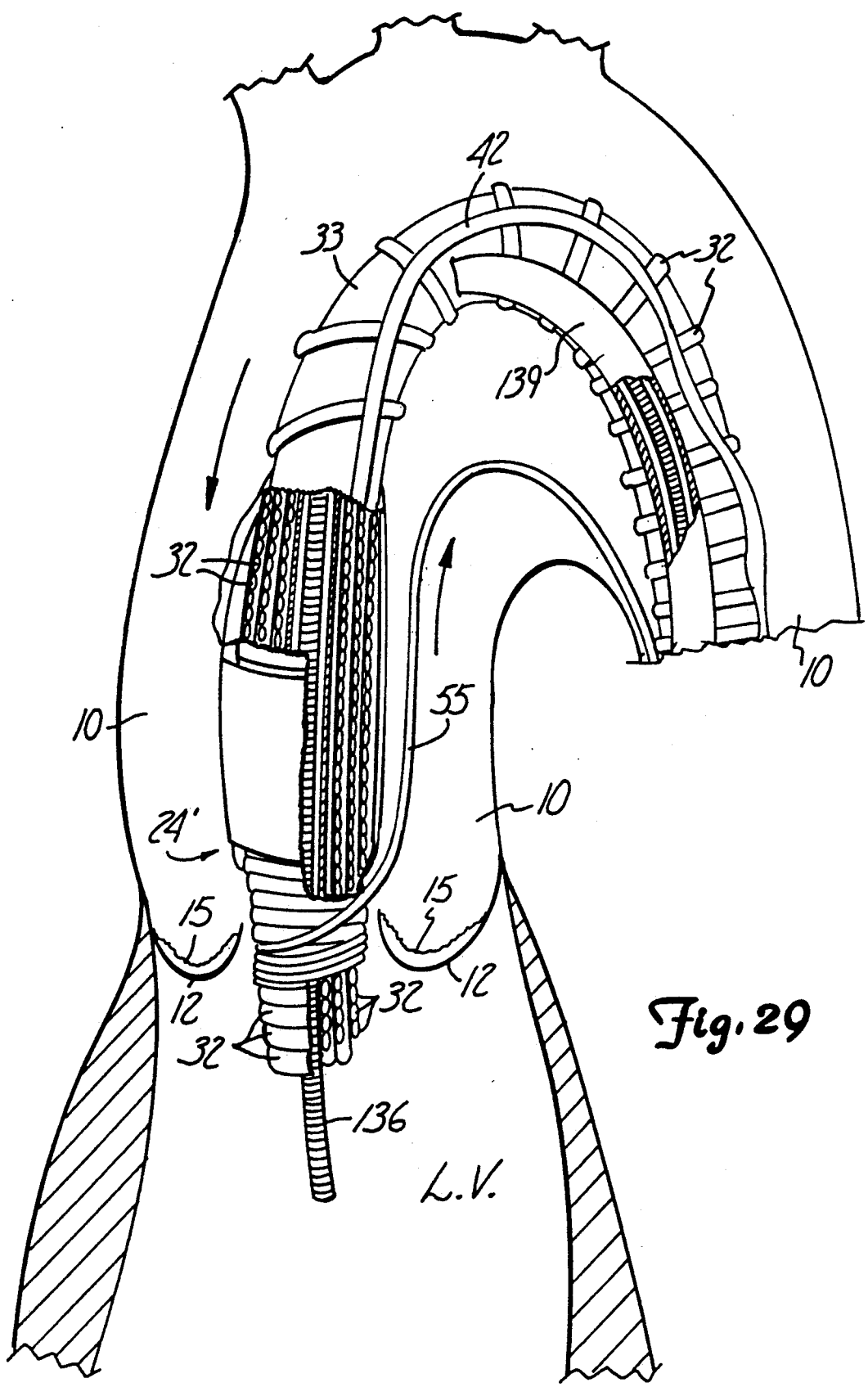
FIG. 29 shows the embodiment of FIG. 27A inserted into position prior to inflation of the anchoring balloon.
Figure 30:
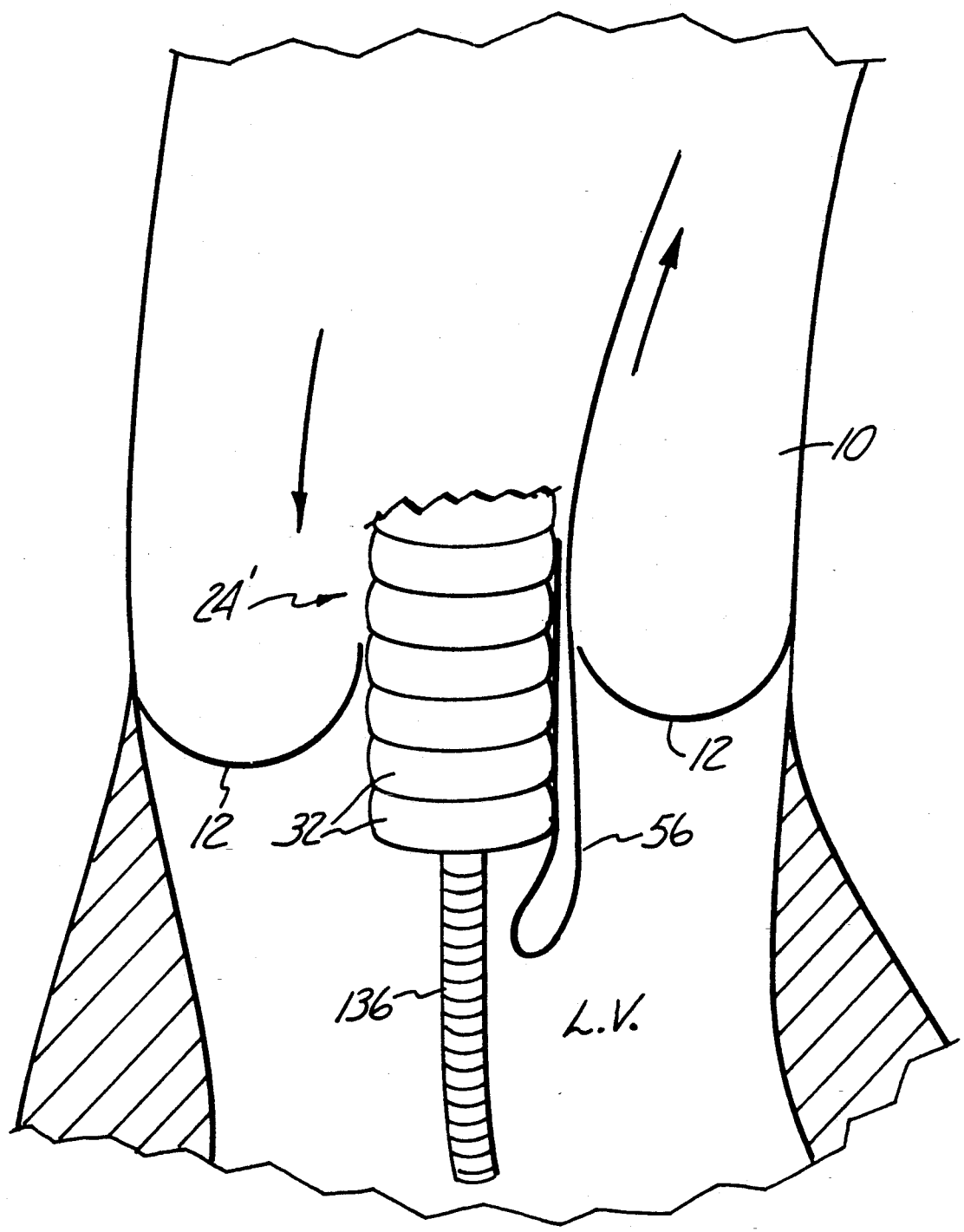
FIG. 30 shows an alternate embodiment, partially broken away, similar to FIG. 29.

FIG. 29 depicts the configuration of the device shown in FIG. 27A and B immediately after it has been advanced over the guide wire 136, but prior to being inflated/unfurled. In FIG. 29, the helical anchoring balloon 24' is in a deflated, furled configuration (the view shows in partial cross-section the layers of helical tubes 32 furled upon one another). A release string 55 may be provided to maintain the distal end of the device in a furled configuration; when the string is withdrawn, it releases the balloon to be inflated. FIG. 30 shows a modified embodiment where a release strap 56 is adhesively attached to the distal portion of the furled helical anchoring balloon 24' (rather than the string 55) to keep it in furled configuration. When the strap is withdrawn, it similarly releases the balloon to be inflated.

Figure 31:
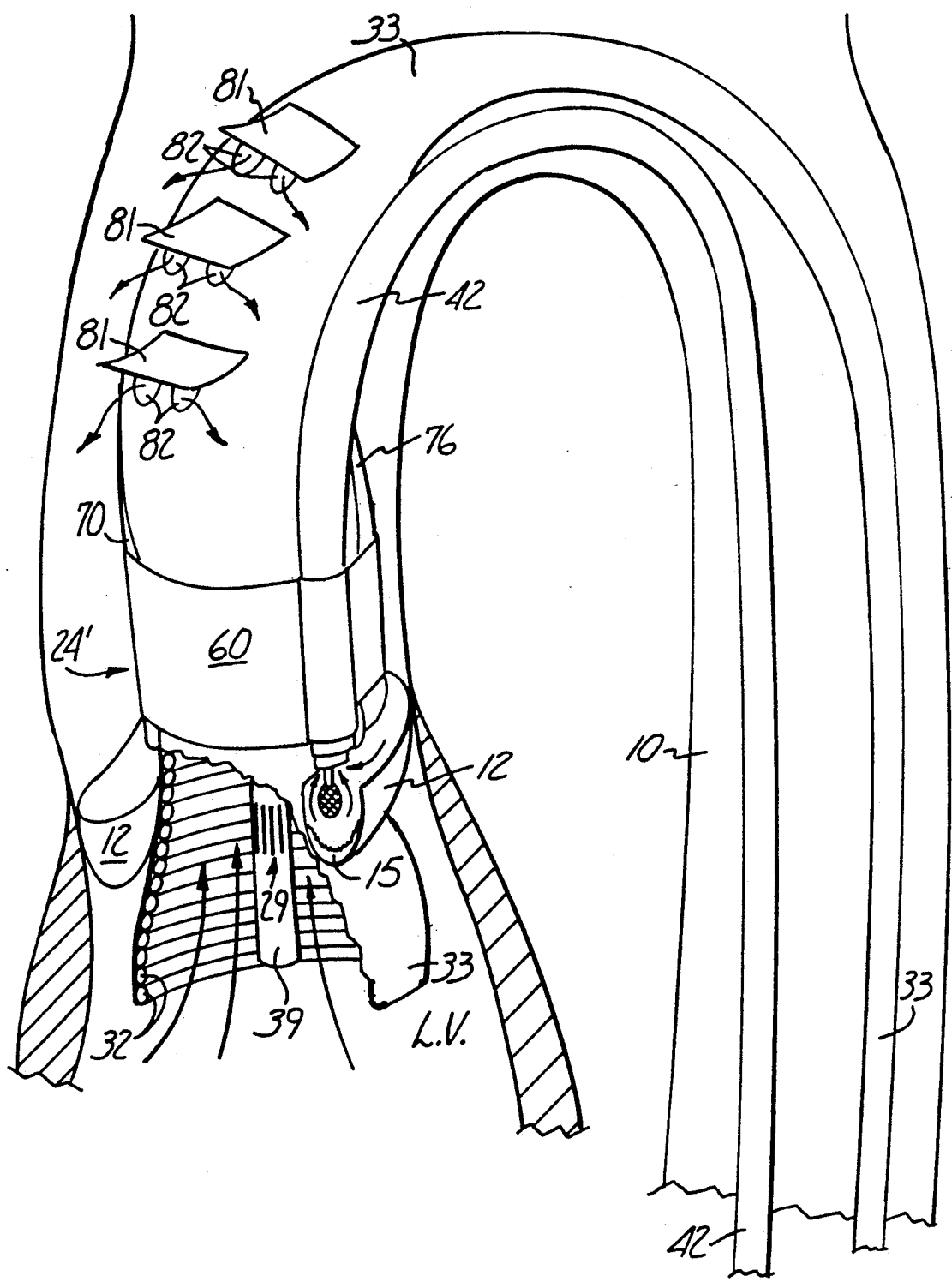
FIG. 31 shows another modified embodiment of the invention.
Figure 32:
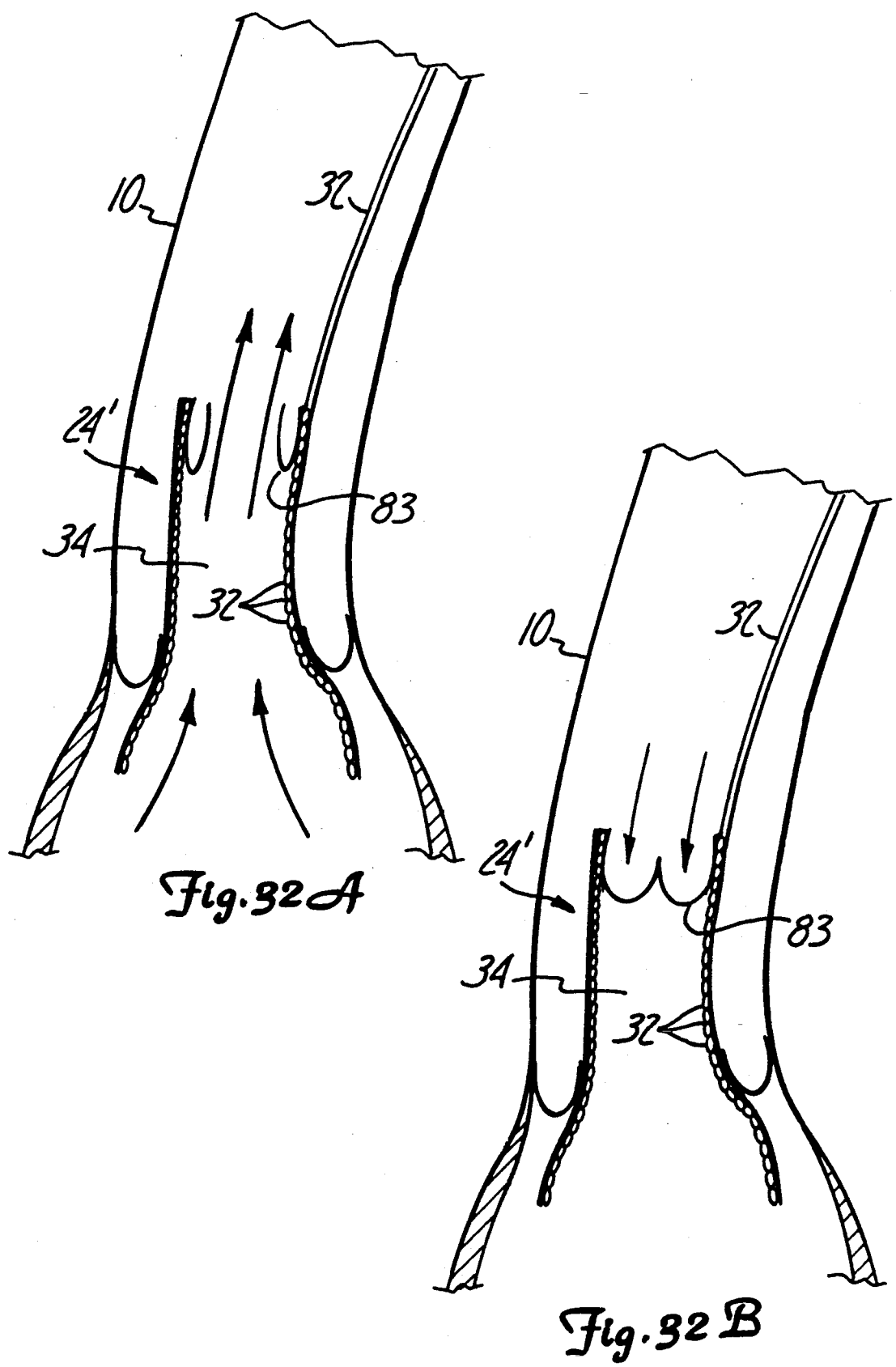
FIGS. 32A and 32B show yet another modified embodiment of the invention.

FIG. 31 depicts yet another embodiment of the invention that facilitates blood flow through the helical anchoring balloon catheter 24' while the procedure is being performed. A series of check valve flaps 81, covering orifices 82 in the skin 33 of the anchoring balloon, is provided proximally of the aortic valve to permit blood to flow outwardly through such orifices 82 into the aorta during systole. During diastole, the valve flaps 81 close, similarly to the function of the aortic valve itself, to prevent reflux of the blood into the left ventricle. (Check valves of this type would also be usable with the anchoring balloon catheter 24 of FIG. 1.) FIGS. 32A and 32B show alternate embodiments wherein the helical anchoring balloon 24' in its proximal portion includes a preferably trileaflet valve 83 similar in shape and function to the natural aortic valve.

Figure 33:
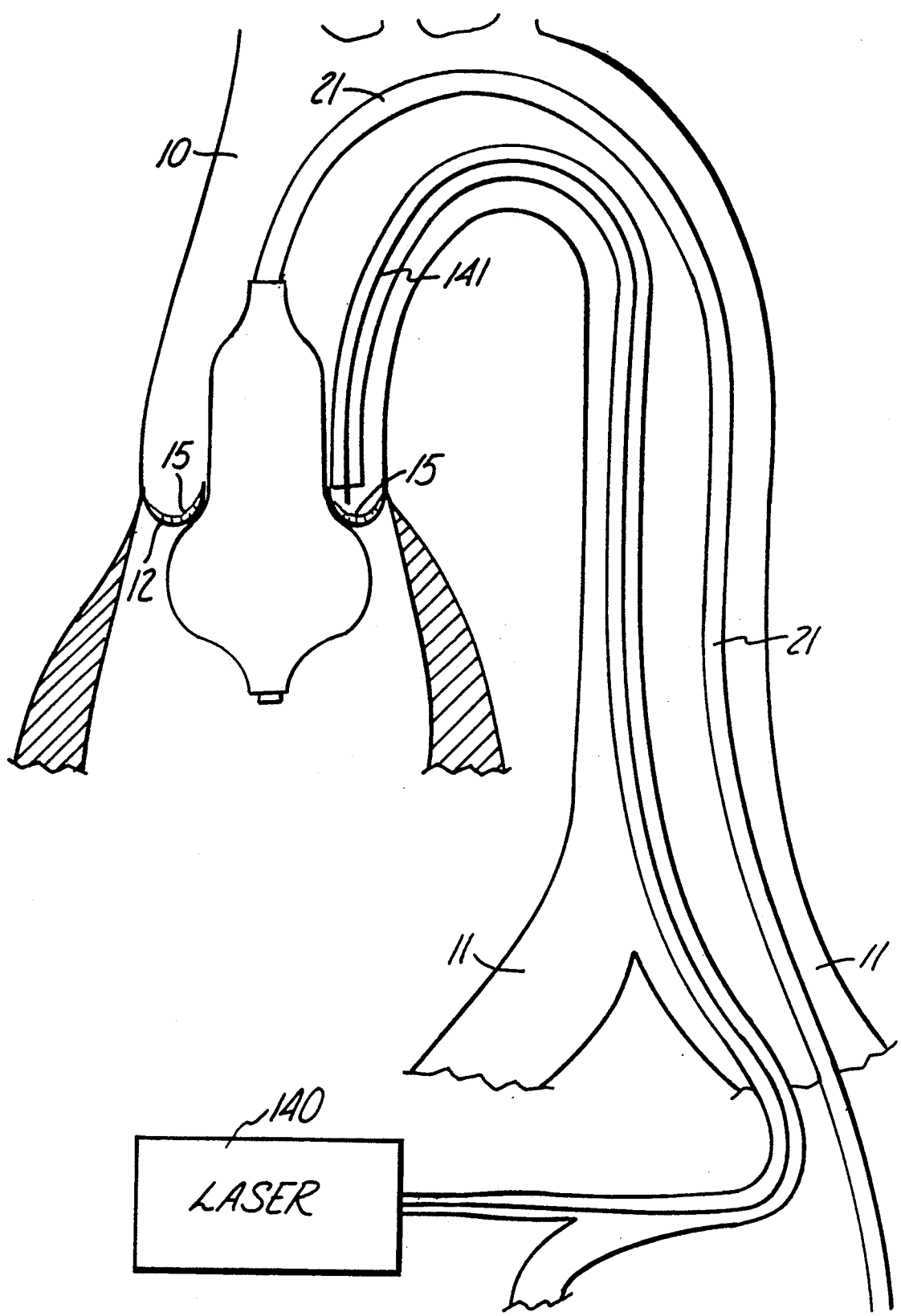
FIGS. 33-35 show alternate deposit removal tools usable with the apparatus of the invention.
Figure 34:
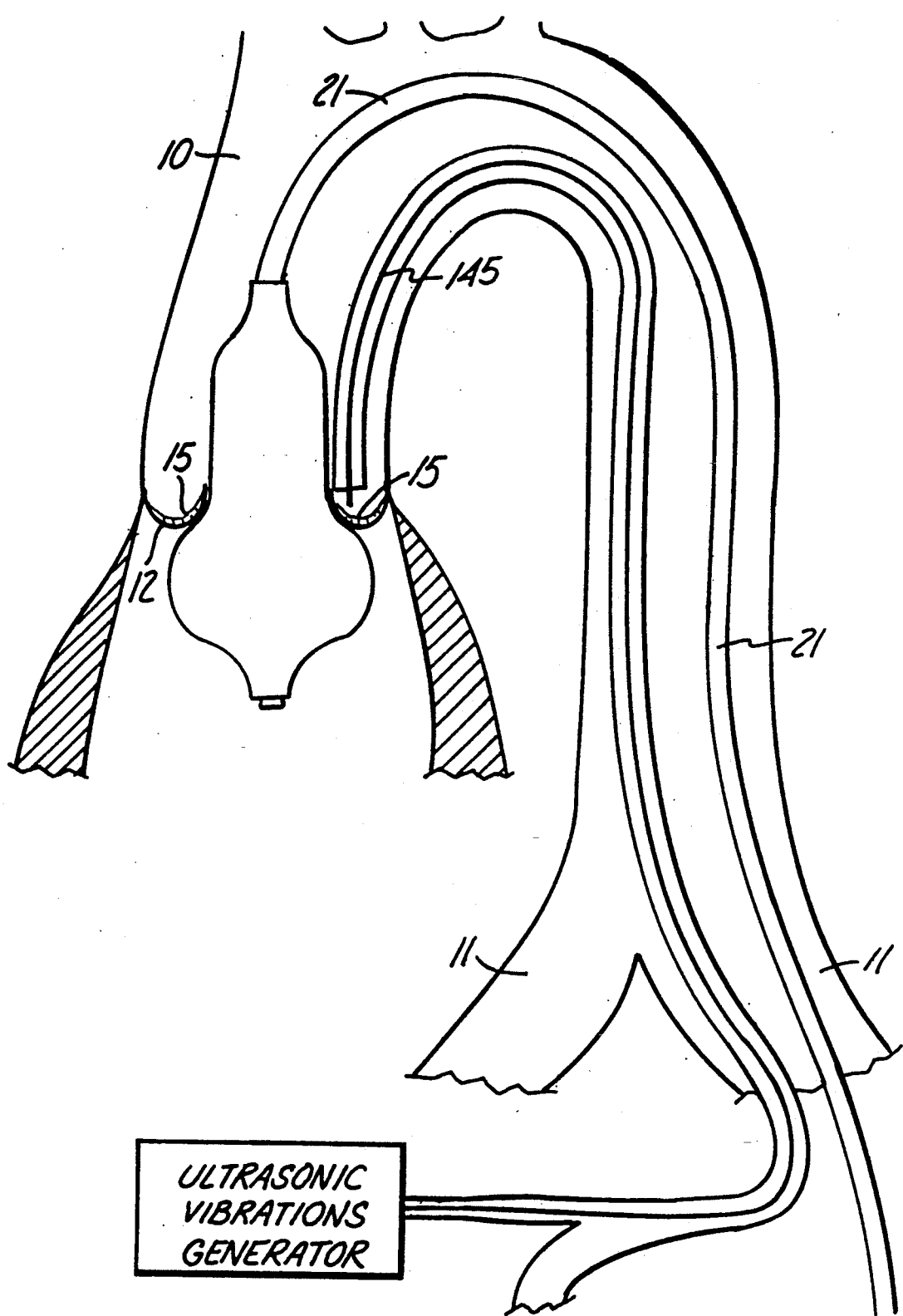
Figure 35:
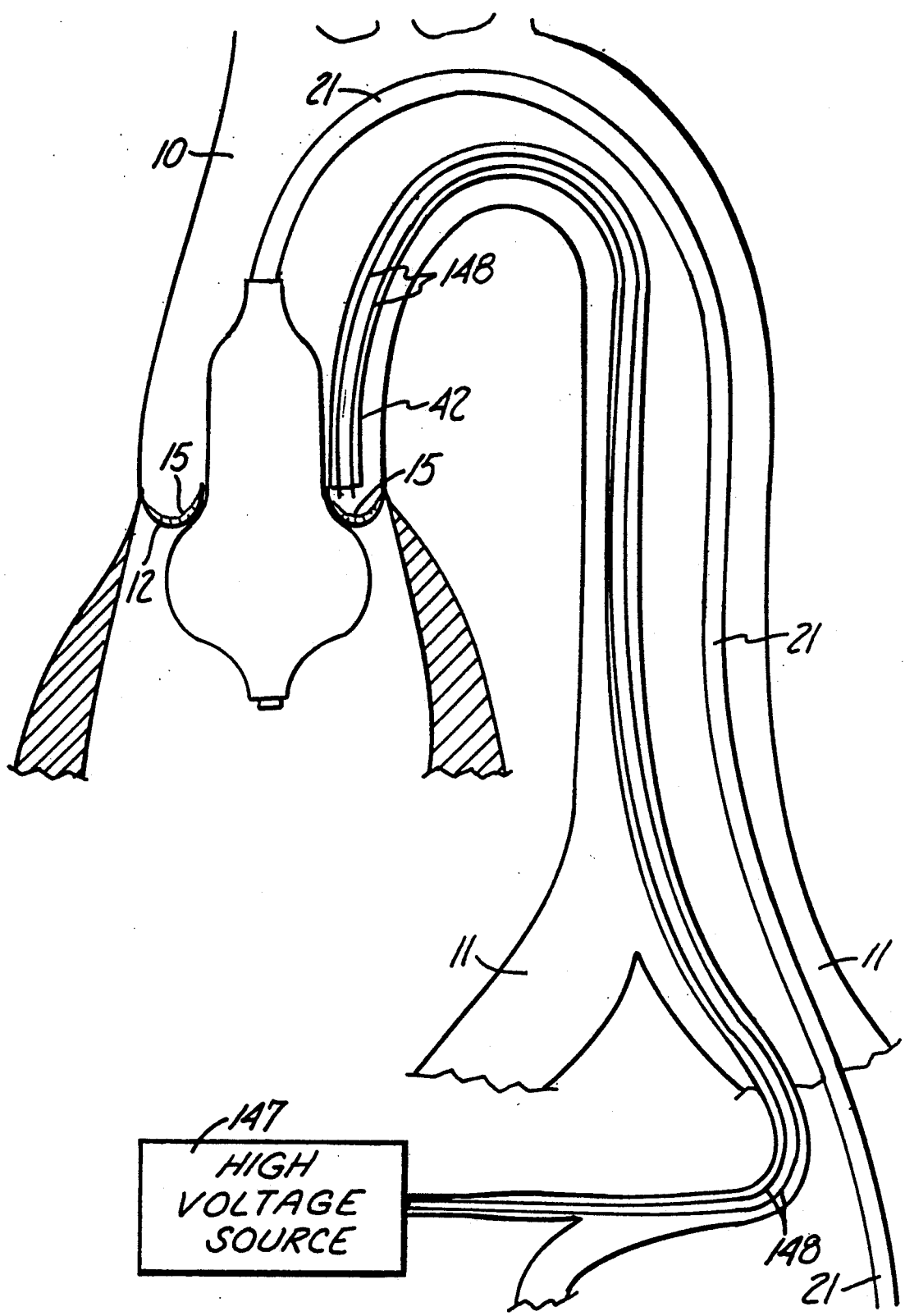

Although most of the figures depict the deposit removal tool as being a conventional rotatable burr or similar cutting or abrasive device, any other suitable tool may also be employed. FIGS. 33-35 depict three other possibilities. In FIG. 33, a laser 140 (preferably located external to the patient) is connected to a fiberoptic strand 141 which has a distal end positionable adjacent the calcified deposits to be removed. In FIG. 34, an ultrasonic vibration generator 144 (e.g., of the type that generates vibrations in the range of 20,000 Hz) is connected to a wire 145 having a distal tip positionable adjacent the calcified deposits, the wire 145 being capable conveying ultrasonic vibrations. In FIG. 35 a high voltage source 147 is connected to a pair of electrically conductive wires 148 having distal tips positionable adjacent the calcified deposits for generating an arc to destroy the deposits. Tools of other suitable configurations may similarly be utilized.

The components of the anchoring balloon catheter 24 of the invention may be manufactured from any suitable materials, including conventional plastics, silicones, etc. that are biocompatible and possess the desired flexibility/rigidity properties, as the case may be, to perform the desired functions. Such materials are well known, being utilized commonly in current balloon catheters and other intravascular devices. The helical balloon of the invention may be manufactured by any suitable techniques, such as by winding tube 32 into a coiled configuration (as by winding it upon a mandrel) and then securing the turns by either applying an outer skin (or an inner skin, if desired). Such a skin may be formed by applying a thin layer of adhesive, by securing a thin layer of flexible plastic, or by any other suitable means.

While a preferred embodiment of the present invention has been described, it should be understood that various changes, adaptations and modifications may be made therein without departing from the spirit of the invention and the scope of the appended claims.

What is claimed is:

1. Apparatus for in vivo removal of deposits from an aortic heart valve, comprising:
   a deposit removal tool; and
   an anchoring balloon catheter fixatable across the aortic valve, the anchoring balloon catheter including anchoring balloon means, having an outer surface, for supporting the valve and for allowing movement of the deposit removal tool in relation to said outer surface, the anchoring balloon means having an inflation lumen extending proximally from the balloon means and including attachment means for securing the tool with respect to the anchoring balloon means and the aortic valve, the attachment means including positioning means for adjustably positioning the deposit removal tool along a range of rotational positions about at least a portion of the outer surface of the anchoring balloon means.

2. The apparatus of claim 1 wherein the attachment means securing the tool to the anchoring balloon means comprises a guiding catheter secured to the anchoring balloon means so as to prevent any substantial movement of the guiding catheter with respect to the anchoring balloon means, the tool being positionable with respect to the aortic valve by rotating the anchoring balloon catheter and by moving the tool within the guiding catheter.

3. Apparatus for in vivo removal of deposits from an aortic heart valve, comprising:
   an anchoring balloon catheter fixatable across the aortic valve;
   a deposit removal tool including an elongated shaft; and
   a guiding catheter through which the deposit removal tool may be advanced toward the aortic valve, the guiding catheter including a distal end portion;
   the anchoring balloon catheter including anchoring balloon means, having an outer surface and being positionable against an inferior surface of the valve, for supporting the valve and for allowing movement of the deposit removal tool in relation to said outer surface, the anchoring balloon means having an inflation lumen extending proximally therefrom, and including attachment means for securing the distal end portion of the guiding catheter to the anchoring balloon means, the attachment means including positioning means for adjustably positioning the deposit removal tool with respect to the anchoring balloon means; and
   a positioning catheter carried within the guiding catheter, the positioning catheter being rotatable with respect to the guiding catheter and including an off-center lumen in which the shaft of the deposit removal tool is closely received, whereby rotation of the positioning catheter allows selective positioning of the deposit removal tool.

4. Apparatus for in vivo removal of deposits from an aortic heart valve of the type having multiple leaflets with superior and inferior surfaces, comprising:
   an anchoring balloon catheter fixatable across the aortic valve including anchoring balloon means, having an outer surface and being positionable against an inferior surface of the valve, for supporting the valve and for allowing movement of the deposit removal tool in relation to said outer surface, the anchoring balloon means having an inflation lumen extending proximally therefrom, and including proximal and distal balloon portions, the distal balloon portion being inflatable to a diameter larger than the proximal balloon portion; and
   a deposit removal tool;
   the anchoring balloon means including attachment means for securing the tool with respect to the anchoring balloon means and the aortic valve;
   the distal and proximal balloon portions defining a shoulder that is engagable with the inferior surface of the valve leaflets to support the leaflets as deposits are removed from the superior surface thereof, the proximal balloon portion being generally elongated and cylindrical in shape and having an outer surface, the shoulder being formed by attaching a secondary distal balloon portion to the outer surface of the proximal balloon portion, the anchoring balloon means having a longitudinal axis, the shoulder portion thereof being made of a stretchable material so that it can conform to the inferior surface of the leaflet, other portions thereof being constructed to be substantially non-stretchable in a direction perpendicular to the longitudinal axis.

5. Apparatus for in vivo removal of deposits from an aortic valve, comprising:
   a deposit removal tool having an elongated shaft;
   a guiding catheter through which the tool may be advanced toward the aortic valve, the guiding catheter including a distal end portion;
   an anchoring balloon catheter fixatable across the aortic valve, including anchoring balloon means, having an outer surface and being positionable against an inferior surface of the valve, for supporting the valve and for allowing movement of the deposit removal tool in relation to said outer surface, the anchoring balloon means having an inflation lumen extending proximally from the balloon and including attachment means for securing the distal end portion of the guiding catheter with respect to the outer surface of the anchoring balloon means, the attachment means comprising:
   a circumferential band having first and second ends respectively attached to the anchoring balloon, and an intermediate portion operatively connected to the guiding catheter;
   a pair of positioning balloons interposed between the circumferential band and the anchoring balloon for selectively moving the guiding catheter about the anchoring balloon in response to inflation and deflation of the positioning balloons; and
   means for selectively inflating and deflating the positioning balloons whereby the guiding catheter will move clockwise about the anchoring balloon means when one of the positioning balloons is inflated, and the guiding catheter will move counterclockwise about the anchoring balloon means when the other positioning balloon is inflated; and
   a positioning catheter carried within the guiding catheter, the positioning catheter being rotatable with respect to the guiding catheter and including an off-center lumen in which the shaft of the deposit removal tool is closely received, whereby rotation of the positioning catheter allows selective positioning of the deposit removal tool.

6. Apparatus for in vivo removal of deposits from an aortic heart valve, comprising:
   a deposit removal tool;
   an anchoring balloon catheter fixatable across the aortic valve, the anchoring balloon catheter including anchoring balloon means having an outer surface and being positionable against an inferior surface of the valve for supporting the valve and for allowing movement of the deposit removal tool in relation to said outer surface, the anchoring balloon means having an inflation lumen extending proximally therefrom and including attachment means for securing the tool with respect to the anchoring balloon means and the aortic valve, the attachment means including positioning means for adjustably positioning the deposit removal tool with respect to the anchoring balloon means; and
a guiding catheter through which the deposit removal tool may be advanced toward the aortic valve, the guiding catheter including a distal end portion secured to the anchoring balloon means by the attachment means;
the attachment means comprising a circumferential band having first and second ends respectively attached to the anchoring balloon means, and an intermediate portion operatively connected to the guiding catheter.

7. The apparatus of claim 6 wherein the attachment means further includes positioning balloon means for selectively moving the guiding catheter about the anchoring balloon means in response to inflation and deflation of the positioning balloon means.

8. The apparatus of claim 7 wherein the positioning balloon means comprises two positioning balloons interposed between the circumferential band and the anchoring balloon means, each positioning balloon including a catheter having an inflation lumen extending proximally therefrom.

9. The apparatus of claim 8 wherein the positioning means includes means for selectively inflating and deflating the positioning balloons whereby the guiding catheter will move clockwise about the anchoring balloon means when one of the positioning balloons is inflated, and the guiding catheter will move counterclockwise about the anchoring balloon means when the other positioning balloon is inflated.

10. The apparatus of claim 9 wherein the means for inflating and deflating the positioning balloons are operable syncronously so that when one of the balloons is being deflated the other is being inflated.

11. The apparatus of claim 8 wherein each positioning balloon is located adjacent an end of the circumferential band.

12. The apparatus of claim 6 including a collapsible guiding catheter insertion sleeve having a distal end portion attached to the intermediate portion of the circumferential band.

13. The apparatus of claim 12 wherein the collapsable insertion sleeve is wider proximally than it is in its distal end portion, so that it receives the guiding catheter closely only in the distal end portion, allowing easy insertion and withdrawal of the guiding catheter through the insertion sleeve.

14. Apparatus for in vivo removal of tissue deposits from a superior surface of a leaflet of an aortic heart valve, comprising:
a deposit removal tool;
a guiding catheter through which the deposit removal tool may be advanced toward the aortic valve, the guiding catheter including a distal end portion; and
an anchoring balloon catheter fixatable across the aortic valve, the anchoring balloon catheter including anchoring balloon means, having an outer surface and being positionable against an inferior surface of the valve leaflet, for supporting the valve leaflet and for allowing movement of the deposit removal tool in relation to said outer surface, the anchoring balloon means having an inflation lumen extending proximally therefrom;
the anchoring balloon means including attachment means for securing the distal end portion of the guiding catheter with respect to the outer surface of the anchoring balloon means and the aortic valve leaflet so that the deposit removal tool can be spaced away from the outer surface of the anchoring balloon, the attachment means being capable of adjustably moving the distal end portion of the guiding catheter, and, thereby, the deposit removal tool around the anchoring balloon means to adjustably position the deposit removal tool over and adjacent to the superior surface of the leaflet when the outer surface of the anchoring balloon means is positioned against the inferior surface of the leaflet, permitting use of the tool to remove tissue from the superior surface of the leaflet.

15. The apparatus of claim 14 further including a cardiopulmonary bypass system comprising a vein access catheter insertable into a vein to allow removal of blood therefrom, oxygenator means for oxygenating such blood, an artery access catheter insertable into an artery, and pump means for returning the blood through the artery access catheter to the artery.

16. The apparatus of claim 15 further including a left ventricle access catheter insertable through the iliac vein, vena cava, through the right atrium and left atrium to the left ventricle, the left ventricle access catheter being operatively connectable to the pump means to allow blood flow from the left ventricle and its return to the artery.

17. The apparatus of claim 16 wherein the vein access catheter and the left ventricle access catheter are arranged in one catheter.

18. The apparatus of claim 17 wherein the vein access catheter and the left ventricle access catheter are arranged in a single lumen catheter having orifices in a wall thereof to define a distal end of the vein access catheter.

19. The apparatus of claim 17 wherein the vein access catheter and the left ventricle access catheter are arranged in a double lumen catheter.

20. The apparatus of claim 17 wherein the vein access catheter and the left ventricle access catheter are arranged in a co-axial double lumen catheter.

21. The apparatus of claim 15 wherein the anchoring balloon catheter includes a catheter having proximal and distal ends and a lumen, the lumen being open at the distal end of the catheter, the proximal end of the catheter lumen being operatively connected to the pump means so that when the anchoring balloon catheter is fixated across the aortic valve blood may be removed through such lumen and returned to the artery.

22. The apparatus of claim 15 wherein the cardiopulmonary bypass system includes a filter and a heat exchanger through which the blood passes before it is returned to the artery.

23. The apparatus of claim 14 wherein the anchoring balloon catheter comprises an inflatable helically coiled tube defining a distally open lumen.

24. The apparatus of claim 23 wherein the helically coiled tube includes a thin skin thereon to hold windings of the helically coiled tube in position with respect to one another.

25. The apparatus of claim 24 wherein the anchoring balloon catheter includes check valve means for permitting blood to flow through the lumen out of the heart's left ventricle and substantially preventing blood from flowing through such lumen back into the left ventricle.

26. The apparatus of claim 25 wherein the check valve means comprises a leaflet-type valve disposed across the lumen of the anchoring balloon catheter.

27. The apparatus of claim 26 wherein the leaflet-type valve is disposed across the lumen at the proximal end of the anchoring balloon catheter.

28. The apparatus of claim 25 wherein the check valve means is disposed on the skin of the helically coiled tube.

29. The apparatus of claim 23 further comprising a screw-type pump means disposed in the lumen for pumping blood across the aortic valve.

30. The apparatus of claim 29 further comprising a second screw-type pump means for withdrawing blood from adjacent the deposit removal tool, and for filtering such blood and returning it to the aorta.

31. The apparatus of claim 30 wherein the second screw-type pump means includes catheter means defining a blood flow path that is operatively isolated from the open lumen of the anchoring balloon catheter and the first screw-type pump means, the catheter means including a distal end located adjacent the deposit removal tool and a proximal portion connected to an inlet of the second screw-type pump means, the second screw-type pump means further including an outlet to the aorta.

32. The apparatus of claim 29 wherein the screw-type pump means comprises two or more screw-type pumps operating in parallel, each having an intake drawing blood distally from the lumen and an outlet discharging the blood proximally into the aorta.

33. The apparatus of claim 14 wherein the anchoring balloon means includes an inflatable balloon having proximal and distal portions, the distal portion of the balloon being inflatable to a diameter larger than the proximal portion.

34. The apparatus of claim 33 wherein the valve is of the type having multiple leaflets with superior and inferior surface, the distal and proximal portions of the balloon defining a shoulder that is engagable with the inferior surface of the valve leaflets to support the leaflets as deposits are removed from the superior surface thereof.

35. The apparatus of claim 34 wherein the proximal portion of the balloon is generally elongated and cylindrical in shape and having an outer surface, the shoulder being formed by attaching a secondary distal balloon portion to the outer surface of the proximal balloon portion.

36. The apparatus of claim 14 wherein the deposit removal tool includes a distal tip portion, an elongated shaft portion extending proximally from the tip, and a catheter disposed about the shaft portion, the catheter having a distal end adjacent the distal tip portion through which dislodged deposits and blood may be aspirated.

37. The apparatus of claim 36 further comprising means for filtering and returning the aspirated blood to the patient.

38. The apparatus of claim 14 wherein the attachment means comprises first and second straps, each having a first end attached to the anchoring balloon means and a second end attached to the guiding catheter, the straps being attached so that as the guiding catheter is rotated with respect to the anchoring balloon means one of the straps will wind up on the guiding catheter and the other will unwind off the guiding catheter, causing the guiding catheter to move about the periphery of the anchoring balloon means.

39. The apparatus of claim 38 wherein the first strap comprises two such straps straddling the second strap.

40. The apparatus of claim 14 wherein the anchoring balloon catheter comprises an inflatable helically coiled tube and securing means for securing windings of the helically coiled tube with respect to one another in a desired configuration.

41. The apparatus of claim 40 wherein the securing means comprises a flexible skin attached to the turns of the coil.

42. The apparatus of claim 14 further including ultrasound transducing means disposed within the anchoring balloon catheter for imaging the aortic valve, the location of the deposit removal tool, and the location of the deposits to be removed.

43. The apparatus of claim 42 wherein the ultrasound transducing means comprises a phased array transducer comprised of an array of individual acoustic elements.

44. The apparatus of claim 42 wherein the ultrasound transducing means comprises an echo transducer and a rotatable mirror element positionable in the anchoring balloon catheter.

45. The apparatus of claim 42 wherein the anchoring balloon catheter includes a catheter lumen, the ultrasound transducing means being carried by a catheter positionable within the lumen of the anchoring balloon catheter and being movable distally and proximally within the lumen.

46. The apparatus of claim 42 wherein the anchoring balloon catheter includes a central catheter, the ultrasound transducing means being carried by the central catheter.

47. The apparatus of claim 14 wherein the attachment means includes positioning means for adjustably positioning the deposit removal tool with respect to the anchoring balloon means.

48. The apparatus of claim 14 wherein the deposit removal tool includes an elongated shaft.

49. The apparatus of claim 14 wherein the deposit removal tool comprises a rotatable cutting device.

50. The apparatus of claim 14 wherein the deposit removal tool comprises a rotatable abrading device.

51. The apparatus of claim 14 wherein the deposit removal tool comprises an ultrasonic vibrations generator and a wire capable of conveying such ultrasonic vibrations connected to the generator and having a distal end locatable adjacent the aortic valve.

52. The apparatus of claim 14 wherein the deposit removal tool comprises a high voltage power source and a pair of electrical discharge electrodes positionable adjacent the aortic valve.

53. The apparatus of claim 14 wherein the deposit removal tool comprises a laser and an optical fiber connected to the laser.

54. The apparatus of claim 14 wherein the positioning means includes a pair of cords attached distally to the anchoring balloon means, and pulleys mounted on the guiding catheter and the anchoring balloon means, the cords being threaded through the pulleys so that pulling on a first of the cords and releasing the second cord will cause the guiding catheter to move clockwise about the anchoring balloon means and, pulling the second cord and releasing the first cord will cause the guiding catheter to move counterclockwise about the anchoring balloon means.

55. The apparatus of claim 14 wherein the anchoring balloon catheter includes a catheter having a distal end and a lumen, the lumen being open at the distal end of the catheter, and has a check valve opening into the aorta.

* * * * *